(12) United States Patent
Sakai et al.

(10) Patent No.: US 7,939,065 B2
(45) Date of Patent: May 10, 2011

(54) CHONDROITIN SULFATE SYNTHESIS PROMOTER

(75) Inventors: Kenichiro Sakai, Tokyo (JP); Koji Kimata, Aichi (JP); Kenichi Shinomiya, Tokyo (JP); Hideto Watanabe, Aichi (JP)

(73) Assignees: Tokyo Medical and Dental University, Tokyo (JP); Seikagaku Corporation, Tokyo (JP)

(*) Notice: Subject to any disclaimer, the term of this patent is extended or adjusted under 35 U.S.C. 154(b) by 68 days.

(21) Appl. No.: 12/313,339

(22) Filed: Nov. 18, 2008

(65) Prior Publication Data

US 2009/0191176 A1 Jul. 30, 2009

Related U.S. Application Data

(62) Division of application No. 11/466,260, filed on Aug. 22, 2006, now abandoned.

(30) Foreign Application Priority Data

Feb. 22, 2006 (JP) .................................. 2006-045813
Aug. 21, 2006 (JP) .................................. 2006-224252

(51) Int. Cl.
*A61K 38/45* (2006.01)
*C12N 9/10* (2006.01)

(52) U.S. Cl. ...................................... 424/94.5; 435/193

(58) Field of Classification Search ................... 435/193; 424/94.5

See application file for complete search history.

(56) References Cited

OTHER PUBLICATIONS

"Acession No. AB081516 and SEQ ID No. 3 alignment", Oct. 10, 2002.

Gotoh et al., "Molecular Cloning and Characterization of a Novel Chondroitin Sulfate Glucuronyltransferase That Transfers Glucuronic Ac", "The Journal of Biological Chemistry", Oct. 11, 2002, pp. 38179-38188, vol. 277, No. 41, Publisher: The American Society for Biochemistry and Molecular Biology, Inc.
Gotoh et al., "Enzymatic Synthesis of Chondroitin with a Novel Chondroitin Sulfate N-Acetylgalactosaminyltransferase That Transfers N-A", "The Journal of Biological Chemistry", Oct. 11, 2002, pp. 38189-38196, vol. 277, No. 41, Publisher: The American Society for Biochemistry and Molecular Biology, Inc.
Kitagawa et al., "Molecular Cloning and Expression of a Human Chondroitin Synthase", "The Journal of Biological Chemistry", Oct. 19, 2001, pp. 38721-38726, vol. 276, No. 42, Publisher: The American Society for Biochemistry and Molecular Biology, Inc.
Sato et al., "Differential Roles of Two N-Acetylgalactosaminyltransferases, CSGaINAct-1, and a Novel Enzyme, CSGaINAcT-2", "The Journal of Biological Chemistry", Jan. 31, 2003, Publisher: The American Society for Biochemistry and Molecular Biology, Inc.
Uyama et al., "Molecular Cloning and Expression of Human Chondroitin N-Acetylgalactosaminyltransferase", "The Journal of Biological Chemistry", , pp. 8841-8846, vol. 277, No. 11, Publisher: The American Society for Biochemistry and Molecular Biology, Inc., (2002).
Yada et al., "Chondroitin Sulfate Synthase-2 Molecular Cloning and Characterization of a Novel Human Glycosyltransferase Homologous to", "The Journal of Biological Chemistry", Aug. 8, 2003, pp. 30235-30247, vol. 278, No. 32, Publisher: The American Society for Biochemistry and Molecular Biology, Inc.
Yada et al., "Chondroitin Sulfate Synthase-3 Molecular Cloning and Characterization", "The Journal of Biological Chemistry", Oct. 10, 2003, pp. 39711-39725, vol. 278, No. 42, Publisher: The American Society for Biochemistry and Molecular Biology, Inc.

*Primary Examiner* — Tekchand Saidha
(74) *Attorney, Agent, or Firm* — Factor & Lake, Ltd.

(57) ABSTRACT

The invention provides a chondroitin sulfate synthesis promoter useful for the treatment of diseases such as articular disease and discopathy. The chondroitin sulfate synthesis promoter contains, as an active ingredient, chondroitin sulfate glucuronyltransferase protein and/or chondroitin sulfate N-acetylgalactosaminyltransferase-1 protein, or a gene encoding the enzyme protein(s).

4 Claims, 22 Drawing Sheets

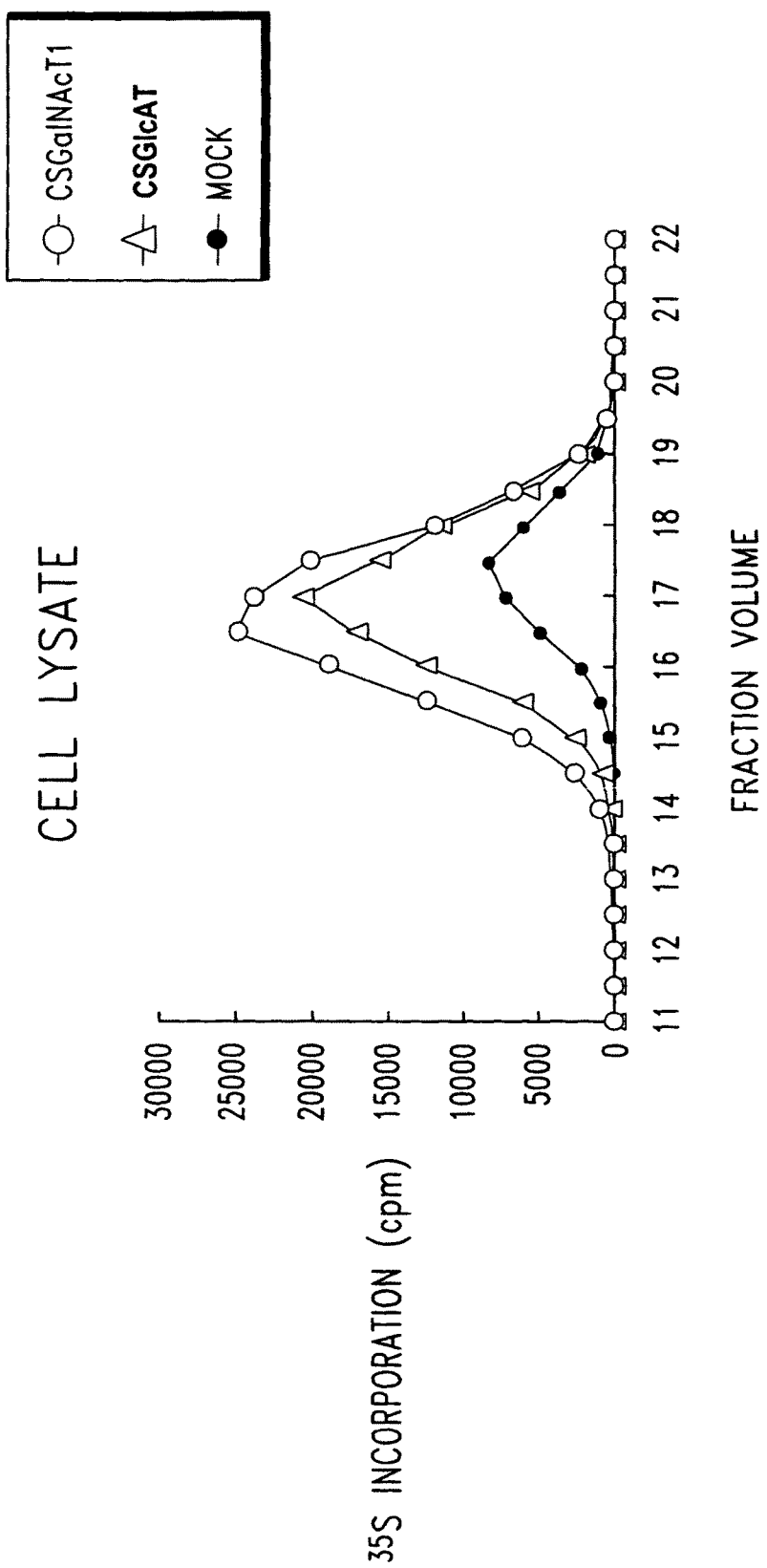
Fig. 7C HSase

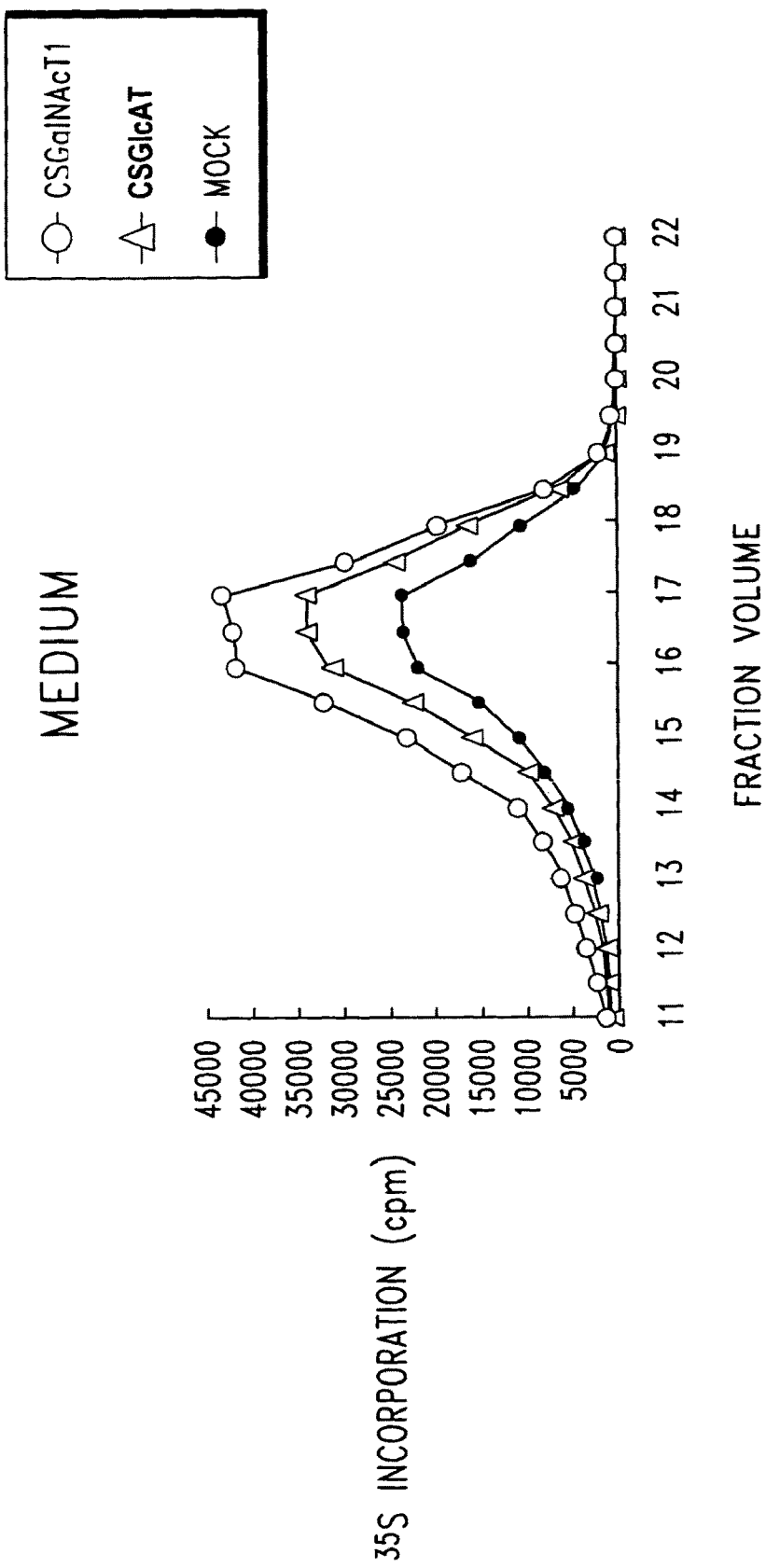
Fig. 7D HSase

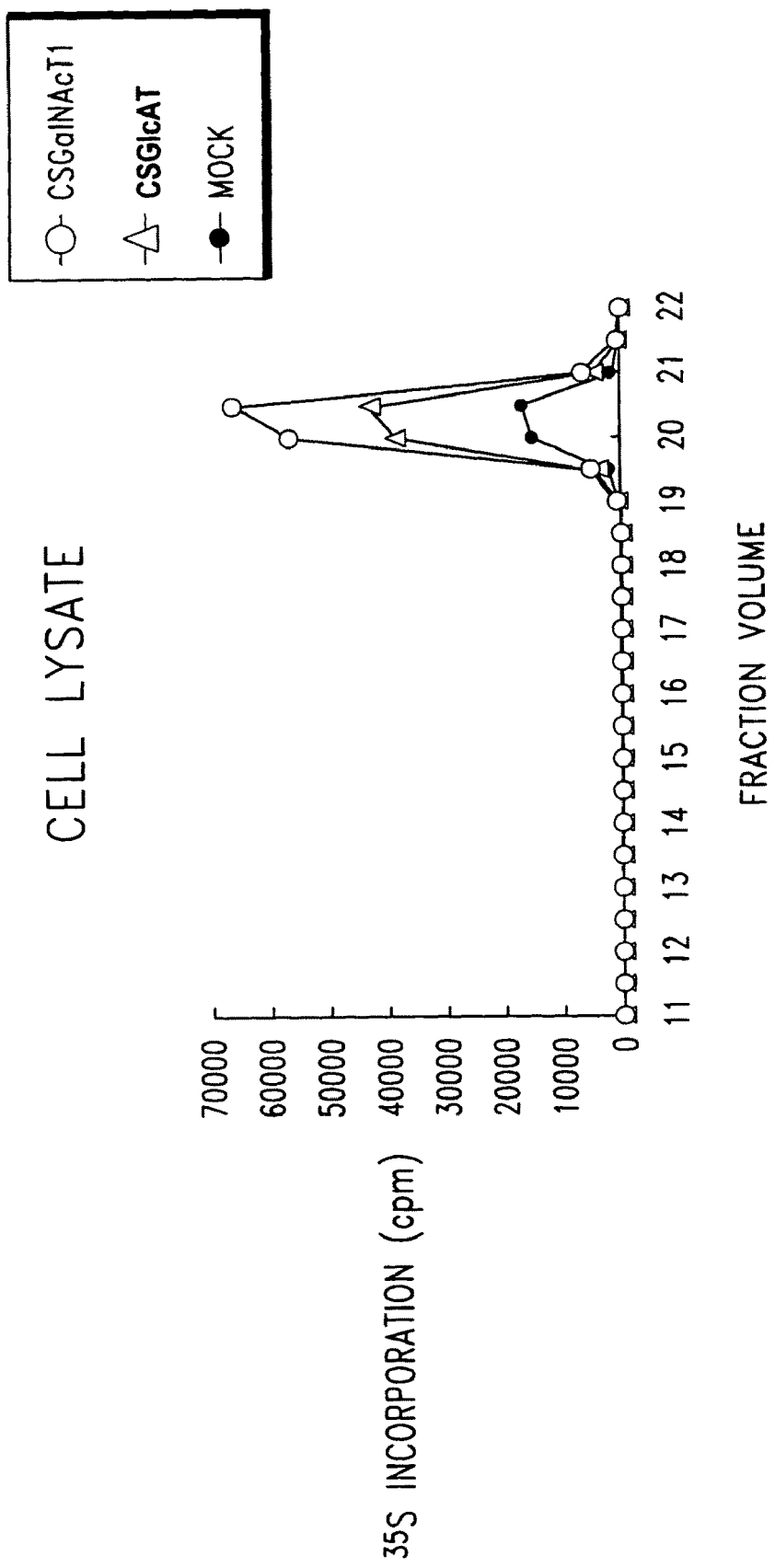
Fig. 7E CHase

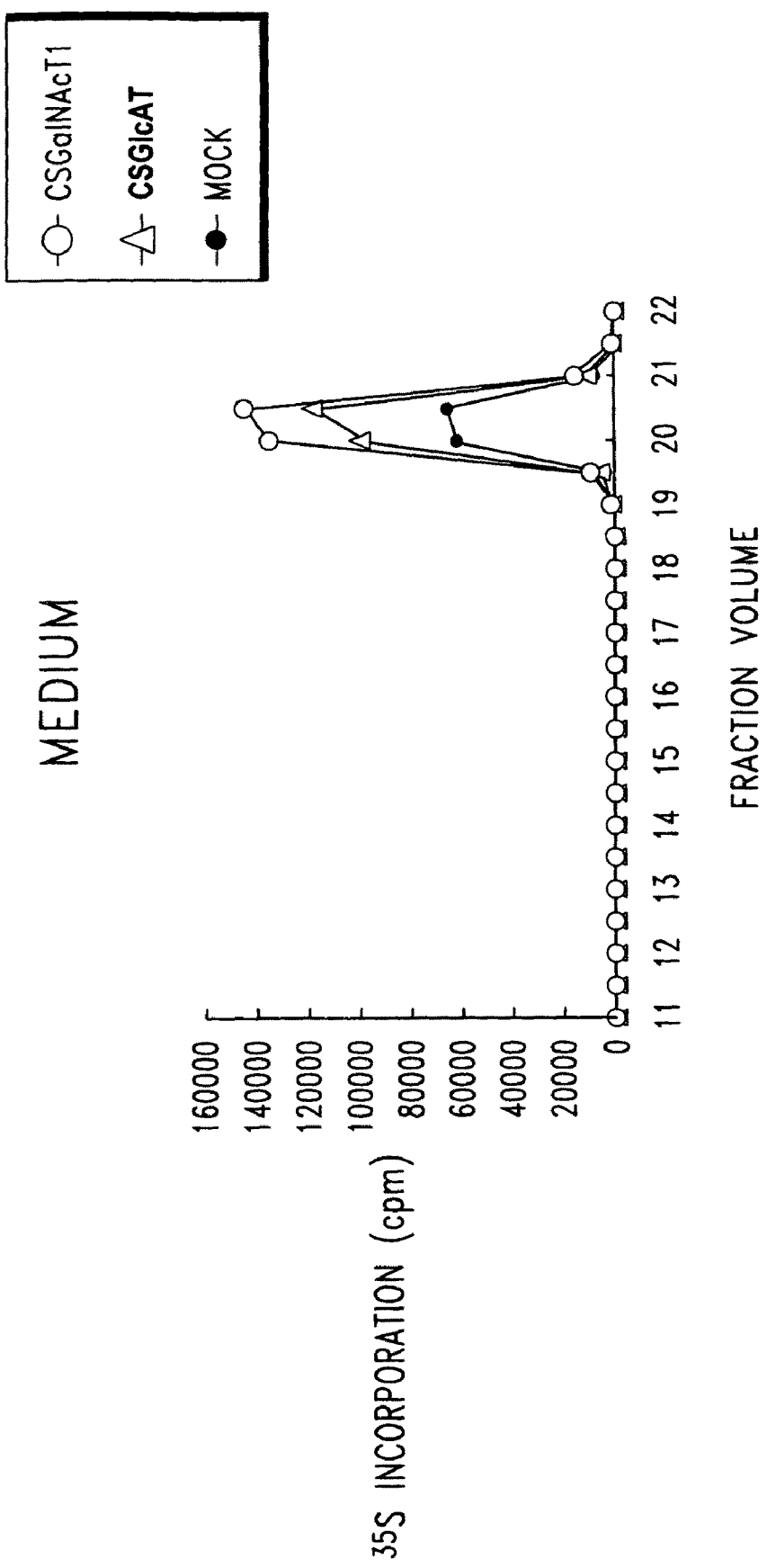
Fig. 7F CHase

SEQUENCE LISTING

<160> NUMBER OF SEQ ID NOS: 39

<210> SEQ ID NO 1
<211> LENGTH: 3970
<212> TYPE: DNA
<213> ORGANISM: Homo sapiens

```
<220> FEATURE:
<221> NAME/KEY: CDS
<222> LOCATION: (1514)..(3829)

<400> SEQUENCE: 1
aggggctgtg aggtggcagc ggctgcagcg gcggagccgg cgcctcagcg ggcactgggg      60
tctgttcccc cttccccgtc cctgctccct gccaggcgcg tgcgggacgc cgctcttggt     120
ccccacgcct ccgccccgcc ccctcccggg acgccgggag accccggccg tcctttatcc     180
ggtgtccgcc ggccccggc cctgaaaccc gggcctcctc cccgagggcc ttgggcgtcc      240
ctcctggtcc tgcgctcgcg gcctcgatgc tgtctctggc gcggcctccg ctcccgccga     300
ctggcctgag aacgaggtct gtgccccagt ctcccagccg cgacctccga ccccgcctcg     360
cagaacgacc cgagctggtc tcccgagccc ccttctcagc agcccggtga cgtgccagt      420 ttatttctgt tttgagacga acggcgaaga ctcgcgtcgg gtcttcgttc tagggctaga     480
cttggtctct gatcgccgag aggtagcgca ggggctgtgg gccccggca ggggtcctgt      540 cggaagctgg ccgcgcttct gtttgcgttc ccaggaccct ggcattgtct ctagttgctg     600
cttgtgctct ctctttgctt ttggtttgct tcatttggcc cctggggccc tggtaaaacc     660
aggcaccgaa tcgctcgcac acagagttcc agtccccgcc tgctgtctcc tcagcagctg     720
gggttccgag gagaatgccc tgcaagatgg ctccatcggc catggcgctc tgagaggct      780 gtcagtgctg agtcaccgat ctacctcatt cgggtgggca gaacttatgt gtgccatgcg     840
agtggctcca gaccgctcct gagtgggagg aggggttcct gtagccgttg cgtcttctca     900
aacacgggga gcagagtaga aagaggctct ggcccttcc cttgtgccca ccgggcctgc      960
cgcagtggct cagcagcccc ttcagtagcc cgcctgagga ccgatgccag aggcaggcat    1020
tcttccggaa aggcccactg aggcaggctc cggctcctct ggttgggct gttgtttga     1080 tggatcgtgt gcttttcct tacctcttat cacttgctgt catctgttga cttaggccca     1140
gtctgcagat gtgtgtagtg ttccttttg ggttagcttt ggcagtattg agttttactt     1200
cctcctcttt ttagtggaag acagaccata atcccagtgt gagtgaaatt gattgtttca     1260
tttattaccg ttttggctgg gggttagttc cgacaccttc acagttgaag agcaggcaga    1320
aggagttgtg aagacaggac aatcttcttg gggatgctgg tcctggaagc cagcgggcct    1380
cgctctgtct ttggcctcat tgaccccagg ttctctggtt aaaactgaaa gcctactact    1440
ggcctggtgc ccatcaatcc attgatcctt gaggctgtgc ccctggggca cccacctggc    1500
agggcctacc acc atg cga ctg agc tcc ctg ttg gct ctg ctg cgg cca        1549
              Met Arg Leu Ser Ser Leu Leu Ala Leu Leu Arg Pro
                1               5                  10 gcg ctt ccc ctc atc tta ggg ctg tct ctg ggg tgc agc ctg agc ctc       1597
Ala Leu Pro Leu Ile Leu Gly Leu Ser Leu Gly Cys Ser Leu Ser Leu
         15                  20                  25 ctg cgg gtt tcc tgg atc cag ggg gag gga gaa gat ccc tgt gtc gag       1645
Leu Arg Val Ser Trp Ile Gln Gly Glu Gly Glu Asp Pro Cys Val Glu
     30                  35                  40 gct gta ggg gag cga gga ggg cca cag aat cca gat tcc aga gct cgg       1693
Ala Val Gly Glu Arg Gly Gly Pro Gln Asn Pro Asp Ser Arg Ala Arg
45                  50                  55                  60 cta gac caa agt gat gaa gac ttc aaa ccc cgg att gtc ccc tac tac       1741
Leu Asp Gln Ser Asp Glu Asp Phe Lys Pro Arg Ile Val Pro Tyr Tyr
                 65                  70                  75 agg gac ccc aac aag ccc tac aag aag gtg ctc agg act cgg tac atc       1789
Arg Asp Pro Asn Lys Pro Tyr Lys Lys Val Leu Arg Thr Arg Tyr Ile
             80                  85                  90
```

```
cag aca gag ctg ggc tcc cgt gag cgg ttg ctg gtg gct gtc ctg acc    1837
Gln Thr Glu Leu Gly Ser Arg Glu Arg Leu Leu Val Ala Val Leu Thr
        95                 100                 105 tcc cga gct aca ctg tcc act ttg gcc gtg gct gtg aac cgt acg gtg    1885
Ser Arg Ala Thr Leu Ser Thr Leu Ala Val Ala Val Asn Arg Thr Val
    110                 115                 120 gcc cat cac ttc cct cgg tta ctc tac ttc act ggg cag cgg ggg gcc    1933
Ala His His Phe Pro Arg Leu Leu Tyr Phe Thr Gly Gln Arg Gly Ala
125                 130                 135                 140 cgg gct cca gca ggg atg cag gtg gtg tct cat ggg gat gag cgg ccc    1981
Arg Ala Pro Ala Gly Met Gln Val Val Ser His Gly Asp Glu Arg Pro
                145                 150                 155 gcc tgg ctc atg tca gag acc ctg cgc cac ctt cac aca cac ttt ggg    2029
Ala Trp Leu Met Ser Glu Thr Leu Arg His Leu His Thr His Phe Gly
        160                 165                 170 gcc gac tac gac tgg ttc ttc atc atg cag gat gac aca tat gtg cag    2077
Ala Asp Tyr Asp Trp Phe Phe Ile Met Gln Asp Asp Thr Tyr Val Gln
    175                 180                 185 gcc ccc cgc ctg gca gcc ctt gct ggc cac ctc agc atc aac caa gac    2125
Ala Pro Arg Leu Ala Ala Leu Ala Gly His Leu Ser Ile Asn Gln Asp
190                 195                 200 ctg tac tta ggc cgg gca gag gag ttc att ggc gca ggc gag cag gcc    2173
Leu Tyr Leu Gly Arg Ala Glu Glu Phe Ile Gly Ala Gly Glu Gln Ala
205                 210                 215                 220 cgg tac tgt cat ggg ggc ttt ggc tac ctg ttg tca cgg agt ctc ctg    2221
Arg Tyr Cys His Gly Gly Phe Gly Tyr Leu Leu Ser Arg Ser Leu Leu
                225                 230                 235 ctt cgt ctg cgg cca cat ctg gat ggc tgc cga gga gac att ctc agt    2269
Leu Arg Leu Arg Pro His Leu Asp Gly Cys Arg Gly Asp Ile Leu Ser
            240                 245                 250 gcc cgt cct gac gag tgg ctt gga cgc tgc ctc att gac tct ctg ggc    2317
Ala Arg Pro Asp Glu Trp Leu Gly Arg Cys Leu Ile Asp Ser Leu Gly
        255                 260                 265 gtc ggc tgt gtc tca cag cac cag ggg cag cag tat cgc tca ttt gaa    2365
Val Gly Cys Val Ser Gln His Gln Gly Gln Gln Tyr Arg Ser Phe Glu
    270                 275                 280 ctg gcc aaa aat agg gac cct gag aag gaa ggg agc tcg gct ttc ctg    2413
Leu Ala Lys Asn Arg Asp Pro Glu Lys Glu Gly Ser Ser Ala Phe Leu
285                 290                 295                 300 agt gcc ttc gcc gtg cac cct gtc tcc gaa ggt acc ctc atg tac cgg    2461
Ser Ala Phe Ala Val His Pro Val Ser Glu Gly Thr Leu Met Tyr Arg
                305                 310                 315 ctc cac aaa cgc ttc agc gct ctg gag ttg gag cgg gct tac agt gaa    2509
Leu His Lys Arg Phe Ser Ala Leu Glu Leu Glu Arg Ala Tyr Ser Glu
            320                 325                 330 ata gaa caa ctg cag gct cag atc cgg aac ctg acc gtg ctg acc ccc    2557
Ile Glu Gln Leu Gln Ala Gln Ile Arg Asn Leu Thr Val Leu Thr Pro
        335                 340                 345 gaa ggg gag gca ggg ctg agc tgg ccc gtt ggg ctc cct gct cct ttc    2605
Glu Gly Glu Ala Gly Leu Ser Trp Pro Val Gly Leu Pro Ala Pro Phe
    350                 355                 360 aca cca cac tct cgc ttt gag gtg ctg ggc tgg gac tac ttc aca gag    2653
Thr Pro His Ser Arg Phe Glu Val Leu Gly Trp Asp Tyr Phe Thr Glu
365                 370                 375                 380 cag cac acc ttc tcc tgt gca gat ggg gct ccc aag tgc cca cta cag    2701
Gln His Thr Phe Ser Cys Ala Asp Gly Ala Pro Lys Cys Pro Leu Gln
                385                 390                 395 ggg gct agc agg gcg gac gtg ggt gat gcg ttg gag act gcc ctg gag    2749
Gly Ala Ser Arg Ala Asp Val Gly Asp Ala Leu Glu Thr Ala Leu Glu
            400                 405                 410
```

| | | |
|---|---|---|
| cag ctc aat cgg cgc tat cag ccc cgc ctg cgc ttc cag aag cag cga<br>Gln Leu Asn Arg Arg Tyr Gln Pro Arg Leu Arg Phe Gln Lys Gln Arg<br>           415                      420                      425 | | 2797 |
| ctg ctc aac ggc tat cgg cgc ttc gac cca gca cgg ggc atg gag tac<br>Leu Leu Asn Gly Tyr Arg Arg Phe Asp Pro Ala Arg Gly Met Glu Tyr<br>     430                            435                       440 | | 2845 |
| acc ctg gac ctg ctg ttg gaa tgt gtg aca cag cgt ggg cac cgg cgg<br>Thr Leu Asp Leu Leu Leu Glu Cys Val Thr Gln Arg Gly His Arg Arg<br>445                      450                       455                   460 | | 2893 |
| gcc ctg gct cgc agg gtc agc ctg ctg cgg cca ctg agc cgg gtg gaa<br>Ala Leu Ala Arg Arg Val Ser Leu Leu Arg Pro Leu Ser Arg Val Glu<br>                 465                       470                     475 | | 2941 |
| atc cta cct atg ccc tat gtc act gag gcc acc cga gtg cag ctg gtg<br>Ile Leu Pro Met Pro Tyr Val Thr Glu Ala Thr Arg Val Gln Leu Val<br>                        480                       485                     490 | | 2989 |
| ctg cca ctc ctg gtg gct gaa gct gct gca gcc ccg gct ttc ctc gag<br>Leu Pro Leu Leu Val Ala Glu Ala Ala Ala Ala Pro Ala Phe Leu Glu<br>     495                            500                       505 | | 3037 |
| gcc ttt gca gcc aat gtc ctg gag cca cga gaa cat gca ttg ctc acc<br>Ala Phe Ala Ala Asn Val Leu Glu Pro Arg Glu His Ala Leu Leu Thr<br>510                      515                       520 | | 3085 |
| ctg ttg ctg gtc tac ggg cca cga gaa ggt ggc cgt gga gct cca gac<br>Leu Leu Leu Val Tyr Gly Pro Arg Glu Gly Gly Arg Gly Ala Pro Asp<br>525                      530                       535                   540 | | 3133 |
| cca ttt ctt ggg gtg aag gct gca gcg gag tta gag cga cgg tac<br>Pro Phe Leu Gly Val Lys Ala Ala Ala Glu Leu Glu Arg Arg Tyr<br>                       545                       550                   555 | | 3181 |
| cct ggg acg agg ctg gcc tgg ctc gct gtg cga gca gag gcc cct tcc<br>Pro Gly Thr Arg Leu Ala Trp Leu Ala Val Arg Ala Glu Ala Pro Ser<br>               560                       565                     570 | | 3229 |
| cag gtg cga ctc atg gac gtg gtc tcg aag aag cac cct gtg gac act<br>Gln Val Arg Leu Met Asp Val Val Ser Lys Lys His Pro Val Asp Thr<br>                 575                       580                     585 | | 3277 |
| ctc ttc ttc ctt acc acc gtg tgg aca agg cct ggg ccc gaa gtc ctc<br>Leu Phe Phe Leu Thr Thr Val Trp Thr Arg Pro Gly Pro Glu Val Leu<br>                       590                       595                     600 | | 3325 |
| aac cgc tgt cgc atg aat gcc atc tct ggc tgg cag gcc ttc ttt cca<br>Asn Arg Cys Arg Met Asn Ala Ile Ser Gly Trp Gln Ala Phe Phe Pro<br>605                      610                       615                   620 | | 3373 |
| gtc cat ttc cag gag ttc aat cct gcc ctg tca cca cag aga tca ccc<br>Val His Phe Gln Glu Phe Asn Pro Ala Leu Ser Pro Gln Arg Ser Pro<br>                       625                       630                   635 | | 3421 |
| cca ggg ccc ccg ggg gct ggc cct gac ccc ccc tcc cct cct ggt gct<br>Pro Gly Pro Pro Gly Ala Gly Pro Asp Pro Pro Ser Pro Pro Gly Ala<br>               640                       645                     650 | | 3469 |
| gac ccc tcc cgg ggg gct cct ata ggg ggg aga ttt gac cgg cag gct<br>Asp Pro Ser Arg Gly Ala Pro Ile Gly Gly Arg Phe Asp Arg Gln Ala<br>                 655                       660                   665 | | 3517 |
| tct gcg gag ggc tgc ttc tac aac gct gac tac ctg gcg gcc cga gcc<br>Ser Ala Glu Gly Cys Phe Tyr Asn Ala Asp Tyr Leu Ala Ala Arg Ala<br>               670                       675                   680 | | 3565 |
| cgg ctg gca ggt gaa ctg gca ggc cag gaa gag gag gaa gcc ctg gag<br>Arg Leu Ala Gly Glu Leu Ala Gly Gln Glu Glu Glu Glu Ala Leu Glu<br>685                      690                       695                   700 | | 3613 |
| ggg ctg gag gtg atg gat gtt ttc ctc cgg ttc tca ggg ctc cac ctc<br>Gly Leu Glu Val Met Asp Val Phe Leu Arg Phe Ser Gly Leu His Leu<br>                       705                       710                   715 | | 3661 |
| ttt cgg gcc gta gag cca ggg ctg gtg cag aag ttc tcc ctg cga gac<br>Phe Arg Ala Val Glu Pro Gly Leu Val Gln Lys Phe Ser Leu Arg Asp<br>                       720                       725                   730 | | 3709 |

```
tgc agc cca cgg ctc agt gaa gaa ctc tac cac cgc tgc cgc ctc agc    3757
Cys Ser Pro Arg Leu Ser Glu Glu Leu Tyr His Arg Cys Arg Leu Ser
        735                 740                 745 aac ctg gag ggg cta ggg ggc cgt gcc cag ctg gct atg gct ctc ttt    3805
Asn Leu Glu Gly Leu Gly Gly Arg Ala Gln Leu Ala Met Ala Leu Phe
    750                 755                 760 gag cag gag cag gcc aat agc act tagcccgcct gggggcccta acctcattac   3859
Glu Gln Glu Gln Ala Asn Ser Thr
765                 770 ctttcctttg tctgcctcag ccccaggaag ggcaaggcaa gatggtggac agatagagaa  3919
ttgttgctgt attttttaaa tatgaaaatg ttattaaaca tgtcttctgc c           3970

<210> SEQ ID NO 2
<211> LENGTH: 772
<212> TYPE: PRT
<213> ORGANISM: Homo sapiens

<400> SEQUENCE: 2

Met Arg Leu Ser Ser Leu Leu Ala Leu Leu Arg Pro Ala Leu Pro Leu
1               5                   10                  15

Ile Leu Gly Leu Ser Leu Gly Cys Ser Leu Ser Leu Arg Val Ser
            20                  25                  30

Trp Ile Gln Gly Glu Gly Glu Asp Pro Cys Val Glu Ala Val Gly Glu
        35                  40                  45

Arg Gly Gly Pro Gln Asn Pro Asp Ser Arg Ala Arg Leu Asp Gln Ser
    50                  55                  60

Asp Glu Asp Phe Lys Pro Arg Ile Val Pro Tyr Tyr Arg Asp Pro Asn
65                  70                  75                  80

Lys Pro Tyr Lys Lys Val Leu Arg Thr Arg Tyr Ile Gln Thr Glu Leu
                85                  90                  95

Gly Ser Arg Glu Arg Leu Leu Val Ala Val Leu Thr Ser Arg Ala Thr
            100                 105                 110

Leu Ser Thr Leu Ala Val Ala Val Asn Arg Thr Val Ala His His Phe
        115                 120                 125

Pro Arg Leu Leu Tyr Phe Thr Gly Gln Arg Gly Ala Arg Ala Pro Ala
    130                 135                 140

Gly Met Gln Val Val Ser His Gly Asp Glu Arg Pro Ala Trp Leu Met
145                 150                 155                 160

Ser Glu Thr Leu Arg His Leu His Thr His Phe Gly Ala Asp Tyr Asp
                165                 170                 175

Trp Phe Phe Ile Met Gln Asp Asp Thr Tyr Val Gln Ala Pro Arg Leu
            180                 185                 190

Ala Ala Leu Ala Gly His Leu Ser Ile Asn Gln Asp Leu Tyr Leu Gly
        195                 200                 205

Arg Ala Glu Glu Phe Ile Gly Ala Gly Glu Gln Ala Arg Tyr Cys His
    210                 215                 220

Gly Gly Phe Gly Tyr Leu Leu Ser Arg Ser Leu Leu Arg Leu Arg
225                 230                 235                 240

Pro His Leu Asp Gly Cys Arg Gly Asp Ile Leu Ser Ala Arg Pro Asp
                245                 250                 255

Glu Trp Leu Gly Arg Cys Leu Ile Asp Ser Leu Gly Val Gly Cys Val
            260                 265                 270

Ser Gln His Gln Gly Gln Gln Tyr Arg Ser Phe Glu Leu Ala Lys Asn
        275                 280                 285

Arg Asp Pro Glu Lys Glu Gly Ser Ser Ala Phe Leu Ser Ala Phe Ala
    290                 295                 300
```

```
Val His Pro Val Ser Glu Gly Thr Leu Met Tyr Arg Leu His Lys Arg
305                 310                 315                 320

Phe Ser Ala Leu Glu Leu Glu Arg Ala Tyr Ser Glu Ile Glu Gln Leu
                325                 330                 335

Gln Ala Gln Ile Arg Asn Leu Thr Val Leu Thr Pro Glu Gly Glu Ala
            340                 345                 350

Gly Leu Ser Trp Pro Val Gly Leu Pro Ala Pro Phe Thr Pro His Ser
        355                 360                 365

Arg Phe Glu Val Leu Gly Trp Asp Tyr Phe Thr Glu Gln His Thr Phe
    370                 375                 380

Ser Cys Ala Asp Gly Ala Pro Lys Cys Pro Leu Gln Gly Ala Ser Arg
385                 390                 395                 400

Ala Asp Val Gly Asp Ala Leu Glu Thr Ala Leu Glu Gln Leu Asn Arg
                405                 410                 415

Arg Tyr Gln Pro Arg Leu Arg Phe Gln Lys Gln Arg Leu Leu Asn Gly
            420                 425                 430

Tyr Arg Arg Phe Asp Pro Ala Arg Gly Met Glu Tyr Thr Leu Asp Leu
        435                 440                 445

Leu Leu Glu Cys Val Thr Gln Arg Gly His Arg Ala Leu Ala Arg
450                 455                 460

Arg Val Ser Leu Leu Arg Pro Leu Ser Arg Val Glu Ile Leu Pro Met
465                 470                 475                 480

Pro Tyr Val Thr Glu Ala Thr Arg Val Gln Leu Val Leu Pro Leu Leu
                485                 490                 495

Val Ala Glu Ala Ala Ala Pro Ala Phe Leu Glu Ala Phe Ala Ala
                500                 505                 510

Asn Val Leu Glu Pro Arg Glu His Ala Leu Leu Thr Leu Leu Leu Val
            515                 520                 525

Tyr Gly Pro Arg Glu Gly Gly Arg Gly Ala Pro Asp Pro Phe Leu Gly
        530                 535                 540

Val Lys Ala Ala Ala Ala Glu Leu Glu Arg Arg Tyr Pro Gly Thr Arg
545                 550                 555                 560

Leu Ala Trp Leu Ala Val Arg Ala Glu Ala Pro Ser Gln Val Arg Leu
                565                 570                 575

Met Asp Val Val Ser Lys Lys His Pro Val Asp Thr Leu Phe Phe Leu
            580                 585                 590

Thr Thr Val Trp Thr Arg Pro Gly Pro Glu Val Leu Asn Arg Cys Arg
        595                 600                 605

Met Asn Ala Ile Ser Gly Trp Gln Ala Phe Phe Pro Val His Phe Gln
    610                 615                 620

Glu Phe Asn Pro Ala Leu Ser Pro Gln Arg Ser Pro Pro Gly Pro Pro
625                 630                 635                 640

Gly Ala Gly Pro Asp Pro Pro Ser Pro Gly Ala Asp Pro Ser Arg
                645                 650                 655

Gly Ala Pro Ile Gly Gly Arg Phe Asp Arg Gln Ala Ser Ala Glu Gly
            660                 665                 670

Cys Phe Tyr Asn Ala Asp Tyr Leu Ala Ala Arg Ala Arg Leu Ala Gly
        675                 680                 685

Glu Leu Ala Gly Gln Glu Glu Glu Ala Leu Glu Gly Leu Glu Val
        690                 695                 700

Met Asp Val Phe Leu Arg Phe Ser Gly Leu His Leu Phe Arg Ala Val
705                 710                 715                 720

Glu Pro Gly Leu Val Gln Lys Phe Ser Leu Arg Asp Cys Ser Pro Arg
                725                 730                 735
```

```
Leu Ser Glu Glu Leu Tyr His Arg Cys Arg Leu Ser Asn Leu Glu Gly
            740                 745                 750

Leu Gly Gly Arg Ala Gln Leu Ala Met Ala Leu Phe Glu Gln Glu Gln
            755                 760                 765

Ala Asn Ser Thr
    770

<210> SEQ ID NO 3
<211> LENGTH: 3426
<212> TYPE: DNA
<213> ORGANISM: Homo sapiens
<220> FEATURE:
<221> NAME/KEY: CDS
<222> LOCATION: (343)..(1938)

<400> SEQUENCE: 3
gagcaatgat gtagccacct cctaaccttc ccttcttgaa cccccaggtc ccctcttgct      60
gttggctgca catcaggaag ctgtgatgg gaatgaaggt gaaaacttgg agatttcact     120
tcagtcattg cttctgcctg caagatcatc ctttaaaagt agagaagctg ctctgtgtgg    180
tggttaactc caagaggcag aactcgttct agaaggaaat ggatgcaagc agctccgggg    240
gccccaaacg catgcttcct gtgatctagc ccagggaagc ccttccgtgg gggccccggc    300
tttgagggat gccaccggtt ctggacgcat ggctgattct ga atg atg atg gtt      354
                                              Met Met Met Val
                                                              1 cgc cgg ggg ctg ctt gcg tgg att tcc cgg gtg gtg gtt ttg ctg gtg     402
Arg Arg Gly Leu Leu Ala Trp Ile Ser Arg Val Val Val Leu Leu Val
 5              10                  15                  20 ctc ctc tgc tgt gct atc tct gtc ctg tac atg ttg gcc tgc acc cca     450
Leu Leu Cys Cys Ala Ile Ser Val Leu Tyr Met Leu Ala Cys Thr Pro
                25                  30                  35 aaa ggt gac gag gag cag ctg gca ctg ccc agg gcc aac agc ccc acg     498
Lys Gly Asp Glu Glu Gln Leu Ala Leu Pro Arg Ala Asn Ser Pro Thr
            40                  45                  50 ggg aag gag ggg tac cag gcc gtc ctt cag gag tgg gag gag cag cac     546
Gly Lys Glu Gly Tyr Gln Ala Val Leu Gln Glu Trp Glu Glu Gln His
        55                  60                  65 cgc aac tac gtg agc agc ctg aag cgg cag atc gca cag ctc aag gag     594
Arg Asn Tyr Val Ser Ser Leu Lys Arg Gln Ile Ala Gln Leu Lys Glu
    70                  75                  80 gag ctg cag gag agg agt gag cag ctc agg aat ggg cag tac caa gcc     642
Glu Leu Gln Glu Arg Ser Glu Gln Leu Arg Asn Gly Gln Tyr Gln Ala
85                  90                  95                 100 agc gat gct gct ggc ctg ggt ctg gac agg agc ccc cca gag aaa acc     690
Ser Asp Ala Ala Gly Leu Gly Leu Asp Arg Ser Pro Pro Glu Lys Thr
                105                 110                 115 cag gcc gac ctc ctg gcc ttc ctg cac tcg cag gtg gac aag gca gag     738
Gln Ala Asp Leu Leu Ala Phe Leu His Ser Gln Val Asp Lys Ala Glu
            120                 125                 130 gtg aat gct ggc gtc aag ctg gcc aca gag tat gca gca gtg cct ttc     786
Val Asn Ala Gly Val Lys Leu Ala Thr Glu Tyr Ala Ala Val Pro Phe
        135                 140                 145 gat agc ttt act cta cag aag gtg tac cag ctg gag act ggc ctt acc     834
Asp Ser Phe Thr Leu Gln Lys Val Tyr Gln Leu Glu Thr Gly Leu Thr
    150                 155                 160 cgc cac ccc gag gag aag cct gtg agg aag gac aag cgg gat gag ttg     882
Arg His Pro Glu Glu Lys Pro Val Arg Lys Asp Lys Arg Asp Glu Leu
165                 170                 175                 180
```

```
gtg gaa gcc att gaa tca gcc ttg gag acc ctg aac aat cct gca gag    930
Val Glu Ala Ile Glu Ser Ala Leu Glu Thr Leu Asn Asn Pro Ala Glu
            185                 190                 195 aac agc ccc aat cac cgt cct tac acg gcc tct gat ttc ata gaa ggg    978
Asn Ser Pro Asn His Arg Pro Tyr Thr Ala Ser Asp Phe Ile Glu Gly
200                 205                 210 atc tac cga aca gaa agg gac aaa ggg aca ttg tat gag ctc acc ttc   1026
Ile Tyr Arg Thr Glu Arg Asp Lys Gly Thr Leu Tyr Glu Leu Thr Phe
            215                 220                 225 aaa ggg gac cac aaa cat gaa ttc aaa cgg ctc atc tta ttt cga cca   1074
Lys Gly Asp His Lys His Glu Phe Lys Arg Leu Ile Leu Phe Arg Pro
230                 235                 240 ttc ggc ccc atc atg aaa gtg aaa aat gaa aag ctc aac atg gcc aac   1122
Phe Gly Pro Ile Met Lys Val Lys Asn Glu Lys Leu Asn Met Ala Asn
245                 250                 255                 260 acg ctt atc aat gtt atc gtg cct cta gca aaa agg gtg gac aag ttc   1170
Thr Leu Ile Asn Val Ile Val Pro Leu Ala Lys Arg Val Asp Lys Phe
            265                 270                 275 cgg cag ttc atg cag aat ttc agg gag atg tgc att gag cag gat ggg   1218
Arg Gln Phe Met Gln Asn Phe Arg Glu Met Cys Ile Glu Gln Asp Gly
            280                 285                 290 aga gtc cat ctc act gtt gtt tac ttt ggg aaa gaa gaa ata aat gaa   1266
Arg Val His Leu Thr Val Val Tyr Phe Gly Lys Glu Glu Ile Asn Glu
            295                 300                 305 gtc aaa gga ata ctt gaa aac act tcc aaa gct gcc aac ttc agg aac   1314
Val Lys Gly Ile Leu Glu Asn Thr Ser Lys Ala Ala Asn Phe Arg Asn
310                 315                 320 ttt acc ttc atc cag ctg aat gga gaa ttt tct cgg gga aag gga ctt   1362
Phe Thr Phe Ile Gln Leu Asn Gly Glu Phe Ser Arg Gly Lys Gly Leu
325                 330                 335                 340 gat gtt gga gcc cgc ttc tgg aag gga agc aac gtc ctt ctc ttt ttc   1410
Asp Val Gly Ala Arg Phe Trp Lys Gly Ser Asn Val Leu Leu Phe Phe
            345                 350                 355 tgt gat gtg gac atc tac ttc aca tct gaa ttc ctc aat acg tgt agg   1458
Cys Asp Val Asp Ile Tyr Phe Thr Ser Glu Phe Leu Asn Thr Cys Arg
            360                 365                 370 ctg aat aca cag cca ggg aag aag gta ttt tat cca gtt ctt ttc agt   1506
Leu Asn Thr Gln Pro Gly Lys Lys Val Phe Tyr Pro Val Leu Phe Ser
            375                 380                 385 cag tac aat cct ggc ata ata tac ggc cac cat gat gca gtc cct ccc   1554
Gln Tyr Asn Pro Gly Ile Ile Tyr Gly His His Asp Ala Val Pro Pro
            390                 395                 400 ttg gaa cag cag ctg gtc ata aag aag gaa act gga ttt tgg aga gac   1602
Leu Glu Gln Gln Leu Val Ile Lys Lys Glu Thr Gly Phe Trp Arg Asp
405                 410                 415                 420 ttt gga ttt ggg atg acg tgt cag tat cgg tca gac ttc atc aat ata   1650
Phe Gly Phe Gly Met Thr Cys Gln Tyr Arg Ser Asp Phe Ile Asn Ile
            425                 430                 435 ggt ggg ttt gat ctg gac atc aaa ggc tgg ggc gga gag gat gtg cac   1698
Gly Gly Phe Asp Leu Asp Ile Lys Gly Trp Gly Gly Glu Asp Val His
            440                 445                 450 ctt tat cgc aag tat ctc cac agc aac ctc ata gtg gta cgg acg cct   1746
Leu Tyr Arg Lys Tyr Leu His Ser Asn Leu Ile Val Val Arg Thr Pro
            455                 460                 465 gtg cga gga ctc ttc cac ctc tgg cat gag aag cgc tgc atg gac gag   1794
Val Arg Gly Leu Phe His Leu Trp His Glu Lys Arg Cys Met Asp Glu
            470                 475                 480 ctg acc ccc gag cag tac aag atg tgc atg cag tcc aag gcc atg aac   1842
Leu Thr Pro Glu Gln Tyr Lys Met Cys Met Gln Ser Lys Ala Met Asn
485                 490                 495                 500
```

-continued

```
gag gca tcc cac ggc cag ctg ggc atg ctg gtg ttc agg cac gag ata      1890
Glu Ala Ser His Gly Gln Leu Gly Met Leu Val Phe Arg His Glu Ile
                505                 510                 515 gag gct cac ctt cgc aaa cag aaa cag aag aca agt agc aaa aaa aca      1938
Glu Ala His Leu Arg Lys Gln Lys Gln Lys Thr Ser Ser Lys Lys Thr
            520                 525                 530 tgaactccca gagaaggatt gtgggagaca cttttctttt cctttttgcaa ttactgaaag   1998 tggctgcaac agagaaaaga cttccataaa ggacgacaaa agaattggac tgatgggtca   2058
gagatgagaa agcctccgat ttctctctgt tgggcttttt acaacagaaa tcaaaatctc   2118
cgctttgcct gcaaaagtaa cccagttgca ccctgtgaag tgtctgacaa aggcagaatg   2178
cttgtgagat tataagccta atggtgtgga ggttttgatg gtgtttacaa tacactgaga   2238
cctgttgttt tgtgtgctca ttgaaatatt catgatttaa gagcagtttt gtaaaaaatt   2298
cattagcatg aaaggcaagc atatttctcc tcatatgaat gagcctatca gcagggctct   2358
agtttctagg aatgctaaaa tatcagaagg caggagagga gataggctta ttatgatact   2418
agtgagtaca ttaagtaaaa taaatggac  cagaaaagaa aagaaaccat aaatatcgtg   2478
tcatattttc cccaagatta accaaaaata atctgcttat cttttttggtt gtccttttaa   2538 ctgtctccgt ttttttcttt tatttaaaaa tgcactttt  ttcccttgtg agttatagtc   2598
tgcttattta attaccactt tgcaagcctt acaagagagc acaagttggc ctacattttt   2658
atatttttta agaagatact ttgagatgca ttatgagaac tttcagttca aagcatcaaa   2718
ttgatgccat atccaaggac atgccaaatg ctgattctgt caggcactga atgtcaggca   2778
ttgagacata gggaaggaat ggtttgtact aatacagacg tacagatact ttctctgaag   2838
agtattttcg aagaggagca actgaacact ggaggaaaag aaaatgacac tttctgctttt  2898 acagaaaagg aaactcattc agactggtga tatcgtgatg tacctaaaag tcagaaacca   2958
cattttctcc tcagaagtag ggaccgcttt cttacctgtt taaataaacc aaagtatacc   3018
gtgtgaacca acaatctct tttcaaaaca gggtgctcct cctggcttct ggcttccata    3078
agaagaaatg gagaaaaata tatatatata tatatatatt gtgaaagatc aatccatctg   3138
ccagaatcta gtgggatgga agtttttgct acatgttatc cacccaggc  caggtggaag   3198 taactgaatt attttttaaa ttaagcagtt ctactcgatc accaagatgc ttctgaaaat   3258
tgcattttat taccatttca aactattttt taaaaataaa tacagttaac atagagtggt   3318
ttcttcattc atgtgaaaat tattagccag caccagatgc atgagctaat tatctctttg   3378
agtccttgct tctgtttgct cacagtaagc tcattgttta aaagcttc                3426
```

<210> SEQ ID NO 4
<211> LENGTH: 532
<212> TYPE: PRT
<213> ORGANISM: Homo sapiens

<400> SEQUENCE: 4

```
Met Met Met Val Arg Gly Leu Leu Ala Trp Ile Ser Arg Val Val
1               5                   10                  15

Val Leu Leu Val Leu Leu Cys Cys Ala Ile Ser Val Leu Tyr Met Leu
                20                  25                  30

Ala Cys Thr Pro Lys Gly Asp Glu Glu Gln Leu Ala Leu Pro Arg Ala
            35                  40                  45

Asn Ser Pro Thr Gly Lys Glu Gly Tyr Gln Ala Val Leu Gln Glu Trp
        50                  55                  60

Glu Glu Gln His Arg Asn Tyr Val Ser Ser Leu Lys Arg Gln Ile Ala
65                  70                  75                  80
```

-continued

```
Gln Leu Lys Glu Glu Leu Gln Glu Arg Ser Glu Gln Leu Arg Asn Gly
             85                  90                  95
Gln Tyr Gln Ala Ser Asp Ala Ala Gly Leu Gly Leu Asp Arg Ser Pro
            100                 105                 110
Pro Glu Lys Thr Gln Ala Asp Leu Leu Ala Phe Leu His Ser Gln Val
        115                 120                 125
Asp Lys Ala Glu Val Asn Ala Gly Val Lys Leu Ala Thr Glu Tyr Ala
    130                 135                 140
Ala Val Pro Phe Asp Ser Phe Thr Leu Gln Lys Val Tyr Gln Leu Glu
145                 150                 155                 160
Thr Gly Leu Thr Arg His Pro Glu Glu Lys Pro Val Arg Lys Asp Lys
                165                 170                 175
Arg Asp Glu Leu Val Glu Ala Ile Glu Ser Ala Leu Glu Thr Leu Asn
            180                 185                 190
Asn Pro Ala Glu Asn Ser Pro Asn His Arg Pro Tyr Thr Ala Ser Asp
        195                 200                 205
Phe Ile Glu Gly Ile Tyr Arg Thr Glu Arg Asp Lys Gly Thr Leu Tyr
    210                 215                 220
Glu Leu Thr Phe Lys Gly Asp His Lys His Glu Phe Lys Arg Leu Ile
225                 230                 235                 240
Leu Phe Arg Pro Phe Gly Pro Ile Met Lys Val Lys Asn Glu Lys Leu
                245                 250                 255
Asn Met Ala Asn Thr Leu Ile Asn Val Ile Pro Leu Ala Lys Arg
            260                 265                 270
Val Asp Lys Phe Arg Gln Phe Met Gln Asn Phe Arg Glu Met Cys Ile
        275                 280                 285
Glu Gln Asp Gly Arg Val His Leu Thr Val Val Tyr Phe Gly Lys Glu
    290                 295                 300
Glu Ile Asn Glu Val Lys Gly Ile Leu Glu Asn Thr Ser Lys Ala Ala
305                 310                 315                 320
Asn Phe Arg Asn Phe Thr Phe Ile Gln Leu Asn Gly Glu Phe Ser Arg
                325                 330                 335
Gly Lys Gly Leu Asp Val Gly Ala Arg Phe Trp Lys Gly Ser Asn Val
            340                 345                 350
Leu Leu Phe Phe Cys Asp Val Asp Ile Tyr Phe Thr Ser Glu Phe Leu
        355                 360                 365
Asn Thr Cys Arg Leu Asn Thr Gln Pro Gly Lys Lys Val Phe Tyr Pro
    370                 375                 380
Val Leu Phe Ser Gln Tyr Asn Pro Gly Ile Ile Tyr Gly His His Asp
385                 390                 395                 400
Ala Val Pro Pro Leu Glu Gln Gln Leu Val Ile Lys Lys Glu Thr Gly
                405                 410                 415
Phe Trp Arg Asp Phe Gly Phe Gly Met Thr Cys Gln Tyr Arg Ser Asp
            420                 425                 430
Phe Ile Asn Ile Gly Gly Phe Asp Leu Asp Ile Lys Gly Trp Gly Gly
        435                 440                 445
Glu Asp Val His Leu Tyr Arg Lys Tyr Leu His Ser Asn Leu Ile Val
    450                 455                 460
Val Arg Thr Pro Val Arg Gly Leu Phe His Leu Trp His Glu Lys Arg
465                 470                 475                 480
Cys Met Asp Glu Leu Thr Pro Glu Gln Tyr Lys Met Cys Met Gln Ser
                485                 490                 495
Lys Ala Met Asn Glu Ala Ser His Gly Gln Leu Gly Met Leu Val Phe
            500                 505                 510
```

```
Arg His Glu Ile Glu Ala His Leu Arg Lys Gln Lys Gln Lys Thr Ser
    515                 520                 525

Ser Lys Lys Thr
    530

<210> SEQ ID NO 5
<211> LENGTH: 17
<212> TYPE: DNA
<213> ORGANISM: Artificial
<220> FEATURE:
<223> OTHER INFORMATION: forward primer

<400> SEQUENCE: 5
ctgcccttgc cccgtaa                                                    17

<210> SEQ ID NO 6
<211> LENGTH: 22
<212> TYPE: DNA
<213> ORGANISM: Artificial
<220> FEATURE:
<223> OTHER INFORMATION: reverse primer

<400> SEQUENCE: 6
gacaggtcaa agatgggctt tg                                              22

<210> SEQ ID NO 7
<211> LENGTH: 22
<212> TYPE: DNA
<213> ORGANISM: Artificial
<220> FEATURE:
<223> OTHER INFORMATION: probe

<400> SEQUENCE: 7
ccctgggcag cgtgatcctc ac                                              22

<210> SEQ ID NO 8
<211> LENGTH: 21
<212> TYPE: DNA
<213> ORGANISM: Artificial
<220> FEATURE:
<223> OTHER INFORMATION: forward primer

<400> SEQUENCE: 8
ctggacctgc tgctcctgta t                                               21

<210> SEQ ID NO 9
<211> LENGTH: 22
<212> TYPE: DNA
<213> ORGANISM: Artificial
<220> FEATURE:
<223> OTHER INFORMATION: reverse primer

<400> SEQUENCE: 9
tcttcaggga attggacagg aa                                              22

<210> SEQ ID NO 10
<211> LENGTH: 29
<212> TYPE: DNA
<213> ORGANISM: Artificial
<220> FEATURE:
<223> OTHER INFORMATION: probe

<400> SEQUENCE: 10
cagcagacct tcagcaagat gcagtttgt                                       29
```

-continued

```
<210> SEQ ID NO 11
<211> LENGTH: 22
<212> TYPE: DNA
<213> ORGANISM: Artificial
<220> FEATURE:
<223> OTHER INFORMATION: forward primer

<400> SEQUENCE: 11
gggctttgga gtcttgctct ct                                                  22

<210> SEQ ID NO 12
<211> LENGTH: 19
<212> TYPE: DNA
<213> ORGANISM: Artificial
<220> FEATURE:
<223> OTHER INFORMATION: reverse primer

<400> SEQUENCE: 12
ggcgagcact gacgatgtc                                                      19

<210> SEQ ID NO 13
<211> LENGTH: 21
<212> TYPE: DNA
<213> ORGANISM: Artificial
<220> FEATURE:
<223> OTHER INFORMATION: probe

<400> SEQUENCE: 13
acagcaactg cgcccccacc t                                                   21

<210> SEQ ID NO 14
<211> LENGTH: 24
<212> TYPE: DNA
<213> ORGANISM: Artificial
<220> FEATURE:
<223> OTHER INFORMATION: forward primer

<400> SEQUENCE: 14
ggaaactggg ttttggagag acta                                                24

<210> SEQ ID NO 15
<211> LENGTH: 25
<212> TYPE: DNA
<213> ORGANISM: Artificial
<220> FEATURE:
<223> OTHER INFORMATION: reverse primer

<400> SEQUENCE: 15
ccgtaagcca gataggatga cttta                                               25

<210> SEQ ID NO 16
<211> LENGTH: 30
<212> TYPE: DNA
<213> ORGANISM: Artificial
<220> FEATURE:
<223> OTHER INFORMATION: probe

<400> SEQUENCE: 16
acggaatcca atgcatttac aaaagcgatc                                          30

<210> SEQ ID NO 17
<211> LENGTH: 16
<212> TYPE: DNA
<213> ORGANISM: Artificial
<220> FEATURE:
<223> OTHER INFORMATION: forward primer
```

-continued

```
<400> SEQUENCE: 17
tggccgtcgc ggttaa                                                    16

<210> SEQ ID NO 18
<211> LENGTH: 21
<212> TYPE: DNA
<213> ORGANISM: Artificial
<220> FEATURE:
<223> OTHER INFORMATION: reverse primer

<400> SEQUENCE: 18
tccatgagac accacctgca t                                              21

<210> SEQ ID NO 19
<211> LENGTH: 32
<212> TYPE: DNA
<213> ORGANISM: Artificial
<220> FEATURE:
<223> OTHER INFORMATION: probe

<400> SEQUENCE: 19
cgtacagtag cacatcactt ccctcggtta ct                                  32

<210> SEQ ID NO 20
<211> LENGTH: 21
<212> TYPE: DNA
<213> ORGANISM: Artificial
<220> FEATURE:
<223> OTHER INFORMATION: forward primer

<400> SEQUENCE: 20
tgagctggta gaagccatcg a                                              21

<210> SEQ ID NO 21
<211> LENGTH: 26
<212> TYPE: DNA
<213> ORGANISM: Artificial
<220> FEATURE:
<223> OTHER INFORMATION: reverse primer

<400> SEQUENCE: 21
gttcggtaaa tcccttctat gaagtc                                         26

<210> SEQ ID NO 22
<211> LENGTH: 26
<212> TYPE: DNA
<213> ORGANISM: Artificial
<220> FEATURE:
<223> OTHER INFORMATION: probe

<400> SEQUENCE: 22
cggccctgga gagtctaaac agccct                                         26

<210> SEQ ID NO 23
<211> LENGTH: 23
<212> TYPE: DNA
<213> ORGANISM: Artificial
<220> FEATURE:
<223> OTHER INFORMATION: forward primer

<400> SEQUENCE: 23
gctgagccag gtaaaaaggt gtt                                            23
```

```
<210> SEQ ID NO 24
<211> LENGTH: 25
<212> TYPE: DNA
<213> ORGANISM: Artificial
<220> FEATURE:
<223> OTHER INFORMATION: reverse primer

<400> SEQUENCE: 24
aaaccagagt ccttttatg aacca                                          25

<210> SEQ ID NO 25
<211> LENGTH: 19
<212> TYPE: DNA
<213> ORGANISM: Artificial
<220> FEATURE:
<223> OTHER INFORMATION: probe

<400> SEQUENCE: 25
caggacgtgc cgccccctg                                                19

<210> SEQ ID NO 26
<211> LENGTH: 28
<212> TYPE: DNA
<213> ORGANISM: Artificial
<220> FEATURE:
<223> OTHER INFORMATION: forward primer

<400> SEQUENCE: 26
ctagaccaaa gtgatgaaga cttcaaac                                      28

<210> SEQ ID NO 27
<211> LENGTH: 22
<212> TYPE: DNA
<213> ORGANISM: Artificial
<220> FEATURE:
<223> OTHER INFORMATION: reverse primer

<400> SEQUENCE: 27
tgtaccgagt cctgagcacc tt                                            22

<210> SEQ ID NO 28
<211> LENGTH: 28
<212> TYPE: DNA
<213> ORGANISM: Artificial
<220> FEATURE:
<223> OTHER INFORMATION: probe

<400> SEQUENCE: 28
ctacagggac cccaacaagc cctacaag                                      28

<210> SEQ ID NO 29
<211> LENGTH: 19
<212> TYPE: DNA
<213> ORGANISM: Artificial
<220> FEATURE:
<223> OTHER INFORMATION: forward primer

<400> SEQUENCE: 29
agcagcaccg caactacgt                                                19

<210> SEQ ID NO 30
<211> LENGTH: 20
<212> TYPE: DNA
<213> ORGANISM: Artificial
<220> FEATURE:
<223> OTHER INFORMATION: reverse primer
```

```
<400> SEQUENCE: 30
ctggcttggt actgcccatt                                              20

<210> SEQ ID NO 31
<211> LENGTH: 23
<212> TYPE: DNA
<213> ORGANISM: Artificial
<220> FEATURE:
<223> OTHER INFORMATION: probe

<400> SEQUENCE: 31
ctgaagcggc agatcgcaca gct                                          23

<210> SEQ ID NO 32
<211> LENGTH: 16
<212> TYPE: DNA
<213> ORGANISM: Artificial
<220> FEATURE:
<223> OTHER INFORMATION: forward primer

<400> SEQUENCE: 32
tggccgtcgc tgttaa                                                  16

<210> SEQ ID NO 33
<211> LENGTH: 21
<212> TYPE: DNA
<213> ORGANISM: Artificial
<220> FEATURE:
<223> OTHER INFORMATION: reverse primer

<400> SEQUENCE: 33
tccatgagac accacctgca t                                            21

<210> SEQ ID NO 34
<211> LENGTH: 32
<212> TYPE: DNA
<213> ORGANISM: Artificial
<220> FEATURE:
<223> OTHER INFORMATION: probe

<400> SEQUENCE: 34
cgtacagtgg cacatcactt ccctcggtta ct                                32

<210> SEQ ID NO 35
<211> LENGTH: 21
<212> TYPE: DNA
<213> ORGANISM: Artificial
<220> FEATURE:
<223> OTHER INFORMATION: forward primer

<400> SEQUENCE: 35
tgagctagtg gaagctatcg a                                            21

<210> SEQ ID NO 36
<211> LENGTH: 26
<212> TYPE: DNA
<213> ORGANISM: Artificial
<220> FEATURE:
<223> OTHER INFORMATION: reverse primer

<400> SEQUENCE: 36
gttcggtaga tcccttctat gaagtc                                       26
```

```
<210> SEQ ID NO 37
<211> LENGTH: 26
<212> TYPE: DNA
<213> ORGANISM: Artificial
<220> FEATURE:
<223> OTHER INFORMATION: probe

<400> SEQUENCE: 37
cagccctgga gagtctaaac agccct                                        26

<210> SEQ ID NO 38
<211> LENGTH: 21
<212> TYPE: DNA
<213> ORGANISM: Artificial
<220> FEATURE:
<223> OTHER INFORMATION: forward primer

<400> SEQUENCE: 38
caccatgatg atggttcgcc g                                             21

<210> SEQ ID NO 39
<211> LENGTH: 24
<212> TYPE: DNA
<213> ORGANISM: Artificial
<220> FEATURE:
<223> OTHER INFORMATION: reverse primer

<400> SEQUENCE: 39 tgttttttg ctacttgtct tctg                                           24
```

CHONDROITIN SULFATE SYNTHESIS PROMOTER

CROSS-REFERENCE TO RELATED APPLICATIONS

This application is a divisional of U.S. application Ser. No. 11/466,260 filed on Aug. 22, 2006, now abandoned which claims priority to Japanese application number 2006-045813, filed on Feb. 22, 2006 and Japanese application number 2006-224252, filed on Aug. 21, 2006, all of which are incorporated herein by reference.

BACKGROUND OF THE INVENTION

1. Field of the Invention

The present invention relates to a chondroitin sulfate synthesis promoter, and to a treatment agent for articular disease and discopathy employing the promoter.

2. Background Art

Cartilage contains a macromolecular substance, called aggrecan, which is predominantly formed of chondroitin sulfate proteoglycan. Aggrecan is a type of proteoglycan in which a polysaccharide sulfate is covalently bound to a core protein, and is known to play an important role in organisms. In cartilage, aggrecan, having a hyaluronic acid-binding domain in a core protein portion, forms a macromolecular complex with a link protein and hyaluronic acid. Aggrecan, having 100 or more chondroitin sulfate chains bound to a core protein portion thereof, retains a large number of water molecules. Thus, aggrecan is present in cartilage in the form of highly hydrated gel and is believed to play important roles such as absorbing shock and reducing friction (lubrication).

Meanwhile, several glycosyltransferases have recently been reported to be involved in synthesis of chondroitin sulfate chains: chondroitin synthase-1 (CSS-1, J. Biol. Chem., October 2001; 276: 38721-38726), chondroitin synthase-2 (CSS-2, J. Biol. Chem., August 2003; 278: 30235-30247, WO 03/102194), chondroitin synthase-3 (CSS-3, J. Biol. Chem., October 2003; 278: 39711-39725, WO 03/102193), chondroitin sulfate glucuronyltransferase (CSGlcAT, J. Biol. Chem., October 2002; 277: No. 41: 38179-38188), chondroitin sulfate N-acetylgalactosaminyltransferase-1 (CSGalNAcT-1, J. Biol. Chem., March 2002; 277: No. 11: 8841-8846), and chondroitin sulfate N-acetylgalactosaminyltransferase-2 (CSGalNAcT-2, J. Biol. Chem., January 2003; 278: 3063-3071, Japanese Patent Application Laid-Open (kokai) No. 2003-289883).

Although general functions of these enzymes are already known, the roles of these enzymes in organisms have not yet been elucidated. In addition, an enzyme involved in biosynthesis of chondroitin sulfate (a part of aggrecan biosynthesis) has not been identified. Therefore, whether or not these enzymes increase the amount of chondroitin sulfate in organisms remains unknown.

SUMMARY OF THE INVENTION

Degradation of cartilage is accelerated by aging or overload. For example, in recent aging society, an increased number of elderly people suffer knee joint pain caused by wear of knee cartilage, leading to keen demand for means of repairing cartilage functions. In cartilage of elderly people, shock absorption performance and friction reduction performance (lubricating action) are considerably impaired. Loss of functions intrinsic to cartilage may predominantly be attributable to a decrease in the amount of chondroitin sulfate chains contained by proteoglycan such as aggrecan. Under such circumstances, the present inventors have attempted to repair and improve functions of cartilage through promoting biosynthesis of chondroitin sulfate chains of aggrecan.

In order to solve the aforementioned object, the present inventors have conducted extensive studies, and have found that among chondroitin sulfate synthesis-related enzymes, chondroitin sulfate glucuronyltransferase (hereinafter sometimes abbreviated as CSGlcAT) and chondroitin sulfate N-acetylgalactosaminyltransferase-1 (hereinafter sometimes referred to as CSGalNAcT-1) are expressed in mouse embryonic cartilage and mouse cartilage differentiated cells in an expression pattern which is considerably correlated with a known aggrecan expression pattern. The inventors have also found that forced over-expression of CSGlcAT and CSGalNAcT-1 in chondroid cells remarkably promotes synthesis of chondroitin sulfate. The inventors have further found that introduction of CSGalNAcT-1 Gene to mouse intervertebral discs increases the levels of chondroitin sulfate in the intervertebral discs, through in vivo experiment.

The present invention has been accomplished on the basis of these findings.

Accordingly, in one aspect of the present invention, there is provided a chondroitin sulfate synthesis promoter comprising, as an active ingredient, a gene encoding chondroitin sulfate glucuronyltransferase and/or a gene encoding chondroitin sulfate N-acetylgalactosaminyltransferase-1.

Preferably, the gene encoding chondroitin sulfate glucuronyltransferase is a nucleic acid molecule selected from at least one of the following:

(a): a nucleic acid molecule including a nucleotide sequence defined by SEQ ID NO: 1, (b): a nucleic acid molecule which can be hybridized with a complement of a nucleic acid of SEQ ID NO: 1 under stringent conditions, or (c): a nucleic acid molecule including a nucleotide sequence identical to that defined by SEQ ID NO: 1, except that one or more nucleotide(s) have been substituted, deleted, inserted, or transposed, wherein the nucleic acid molecule encodes a protein having activity of transferring glucuronate from a glucuronate donor to a non-reducing end N-acetylgalactosamine residue present in the chondroitin skeleton.

Preferably, the chondroitin sulfate synthesis promoter comprises, as an active ingredient, a nucleic acid molecule including a nucleotide sequence encoding an amino acid sequence defined by SEQ ID NO: 2.

Preferably, the gene encoding chondroitin sulfate N-acetylgalactosaminyltransferase-1 is a nucleic acid molecule selected from at least one of the following:

(d): a nucleic acid molecule including a nucleotide sequence defined by SEQ ID NO: 3, (e): a nucleic acid molecule which can be hybridized with a complement of a nucleic acid of SEQ ID NO: 3 under stringent conditions, or (f): a nucleic acid molecule including a nucleotide sequence identical to that defined by SEQ ID NO: 3, except that one or more nucleotide(s) have been substituted, deleted, inserted, or transposed, wherein the nucleic acid molecule encodes a protein having activity of transferring an N-acetylgalactosamine residue from an N-acetylgalactosamine donor to a non-reducing end D-glucuronate residue of an N-acetylgalactosamine acceptor substrate containing a sugar chain represented by formula;

GlcUA-Gal-Gal-Xyl (wherein GlcUA represents a D-glucuronate residue, Gal represents a D-galactose residue, Xyl represents a D-xylose residue, and "-" represents a glycosidic linkage).

Preferably, the chondroitin sulfate synthesis promoter comprises, as an active ingredient, a nucleic acid molecule including a nucleotide sequence encoding an amino acid sequence defined by SEQ ID NO: 4.

In another aspect of the present invention, there is provided a chondroitin sulfate synthesis promoter comprising, as an active ingredient, chondroitin sulfate glucuronyltransferase and/or chondroitin sulfate N-acetylgalactosaminyltransferase-1.

Preferably, the chondroitin sulfate glucuronyltransferase is an enzyme selected from at least one of the following:

(A): an enzyme comprising a protein which includes an amino acid sequence defined by SEQ ID NO: 2, or (B): an enzyme comprising a protein which includes an amino acid sequence identical to that defined by SEQ ID NO: 2, except that one or more amino acid residue(s) have been substituted, deleted, inserted, or transposed, wherein the protein has activity of transferring glucuronate from a glucuronate donor to a non-reducing end N-acetylgalactosamine residue present in the chondroitin skeleton.

Preferably, the chondroitin sulfate N-acetylgalactosaminyltransferase-1 is an enzyme selected from at least one of the following:

(C): an enzyme comprising a protein which includes an amino acid sequence defined by SEQ ID NO: 4, or (D): an enzyme comprising a protein which includes an amino acid sequence identical to that defined by SEQ ID NO: 4, except that one or more amino acid residue(s) have been substituted, deleted, inserted, or transposed, wherein the protein has activity of transferring an N-acetylgalactosamine residue from an N-acetylgalactosamine donor to a non-reducing end D-glucuronate residue of an N-acetylgalactosamine acceptor substrate containing a sugar chain represented by formula;

GlcUA-Gal-Gal-Xyl (wherein GlcUA represents a D-glucuronate residue, Gal represents a D-galactose residue, Xyl represents a D-xylose residue, and "-" represents a glycosidic linkage).

Preferably, the gene encoding chondroitin sulfate glucuronyltransferase and a gene encoding chondroitin sulfate N-acetylgalactosaminyltransferase-1 are incorporated into an expression vector or a host cell.

In yet another aspect of the present invention, there is provided a treatment agent for articular disease and discopathy employing, as an active ingredient, any of the chondroitin sulfate synthesis promoters.

The chondroitin sulfate synthesis promoter according to the present invention can promote synthesis of chondroitin sulfate contained in proteoglycan such as aggrecan. Therefore, the synthesis promoter is suitable for improving cartilage functions and treating articular disease and discopathy.

Accordingly, the present invention provides a method for promoting chondroitin sulfate synthesis in a living subject wherein the living subject includes a joint, a cartilage, an intervertebral disc or a cell, the method comprising the steps of:

providing a gene comprising a gene encoding chondroitin sulfate glucuronyltransferase or a gene encoding chondroitin sulfate N-acetylgalactosaminyltransferase-1; and introducing the gene into the living subject.

Preferably, the step of introducing the gene into the living subject is performed with a gene gun or via injection.

Further, the present invention provides a method for promoting a chondroitin sulfate synthesis in a living subject wherein the living subject includes a joint, a cartilage, an intervertebral disc or a cell, the method comprising the steps of:

providing a chondroitin sulfate glucuronyltransferase or chondroitin sulfate N-acetylgalactosaminyltransferase-1; and introducing a chondroitin sulfate glucuronyltransferase or chondroitin sulfate N-acetylgalactosaminyltransferase-1 into the living subject.

Preferably, the step of introducing a chondroitin sulfate glucuronyltransferase or chondroitin sulfate N-acetylgalactosaminyltransferase-1 into the living subject is performed via injection.

Further, the present invention provides a method for treating an articular disease or discopathy, the method comprising the steps of:

applying a therapeutically effective amount of an active ingredient comprising a chondroitin sulfate glucuronyltransferase, a gene encoding chondroitin sulfate glucuronyltransferase, a chondroitin sulfate N-acetylgalactosaminyltransferase-1, and/or a gene encoding a chondroitin sulfate N-acetylgalactosaminyltransferase-1 with the affected joint or intervertebral disc; and promoting a chondroitin sulfate synthesis in the affected joint or intervertebral disc.

These and other objects/aspects of the present invention will become apparent in light of the present specification, claims and drawings appended hereto.

BEST MODE FOR PRACTICING THE INVENTION

Figure 1:
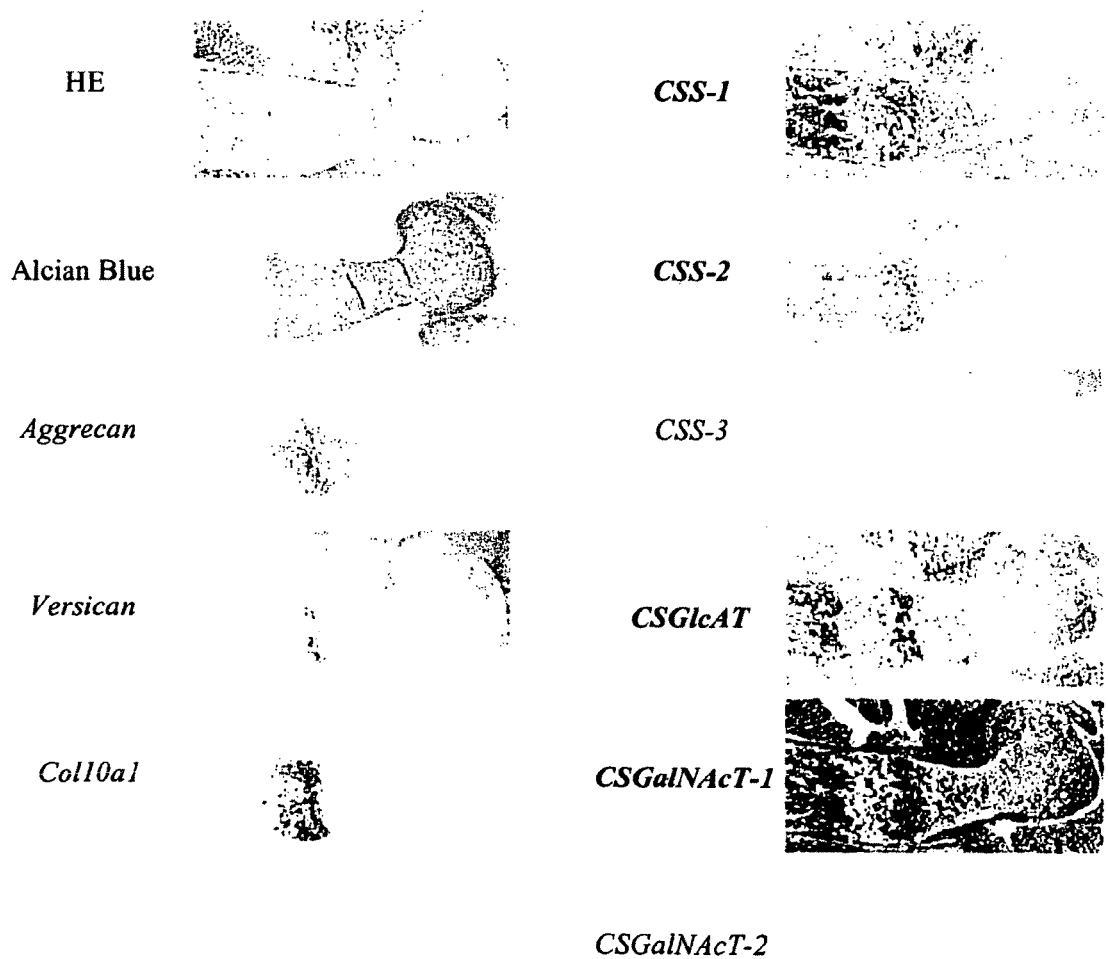
FIG. 1 shows in situ hybridization results to confirm expression of chondroitin sulfate glycosyltransferases in cartilage (photographs)

While this invention is susceptible of embodiment in many different forms, there is shown in the drawings and will be described in detail, several specific embodiments with the understanding that the present disclosure is to be considered as an exemplification of the principles of the invention and is not intended to limit the invention to the embodiments illustrated.

In a first embodiment of the invention, the chondroitin sulfate synthesis promoter contains, as an active ingredient, a gene encoding chondroitin sulfate glucuronyltransferase and/or a gene encoding chondroitin sulfate N-acetylgalactosaminyltransferase-1.

Examples of the gene coding for chondroitin sulfate glucuronyltransferase (CSGlcAT) include a nucleic acid molecule including a nucleotide sequence defined by SEQ ID NO: 1 and encoding human CSGlcAT. The nucleic acid molecule may be obtained through, for example, isolating RNA from human bone culture cells or similar cells and performing RT-PCR by use of a primer design based on SEQ ID NO: 1.

The gene encoding CSGlcAT is not limited to a nucleic acid including a nucleotide sequence defined by SEQ ID NO: 1. So long as the nucleic acid molecule encodes a protein having CSGlcAT activity, there may be employed a nucleic acid molecule which can be hybridized with a complement of a nucleic acid of SEQ ID NO: 1 under stringent conditions. The stringent conditions include routine washing conditions employed in southern blotting; e.g., 65° C., 0.1×SSC, 0.1% SDS solution.

So long as the nucleic acid molecule encodes a protein having CSGlcAT activity, the gene encoding CSGlcAT may be a nucleic acid molecule including a nucleotide sequence identical to that defined by SEQ ID NO: 1, except that one or more nucleotide(s) have been substituted, deleted, inserted, or transposed. The number of such nucleotides is preferably 2 to 20, more preferably 2 to 10, particularly preferably 2 to 5.

The gene encoding CSGlcAT also includes a nucleic acid which has a high sequence identity (including as preferable examples, 75-100%, 80-100%, or 90-100% sequence identity, or 91%, 92%, 93%, 94%, 95%, 96%, 97%, 98%, 99%, 99.5%, or 99.9% sequence identity; higher sequence identities are more preferable among the above examples) to a nucleotide sequence defined by SEQ ID NO: 1.

The aforementioned homologue genes include naturally occurring species-dependent variants and variants produced through treatment such as UV irradiation or treatment with a variation-inducing agent. The gene encoding CSGlcAT may be a gene derived from a non-human organism. However, when the product is employed as a drug for human use, a human-derived gene is preferred. Thus, the gene encoding CSGlcAT may be a nucleic acid molecule including a nucleotide sequence encoding an amino acid sequence defined by SEQ ID NO: 2.

As used herein, the term "CSGlcAT activity" refers to activity of transferring glucuronate from a glucuronate donor to a non-reducing end N-acetylgalactosamine residue present in the chondroitin skeleton. The activity may be determined through a method disclosed in J. Biol. Chem. 2002 Oct. 11; 277 (41): 38179-88.

Examples of the gene encoding chondroitin sulfate N-acetylgalactosaminyltransferase-1 (CSGalNAcT-1) include a nucleic acid molecule including a nucleotide sequence defined by SEQ ID NO: 3 and encoding human CSGalNAcT-1. The nucleic acid molecule may be obtained through, for example, isolating RNA from human bone culture cells or similar cells and performing RT-PCR by use of a primer design on the basis of SEQ ID NO: 3.

The gene encoding CSGalNAcT-1 is not limited to a nucleic acid including a nucleotide sequence defined by SEQ ID NO: 3. So long as the nucleic acid molecule encodes a protein exhibiting CSGalNAcT-1 activity, a nucleic acid molecule which can be hybridized with a complement of a nucleic acid of SEQ ID NO: 3 under stringent conditions may be employed. The stringent conditions include routine washing conditions employed in southern blotting; e.g., 65° C., 0.1× SSC, 0.1% SDS solution.

So long as the nucleic acid molecule encodes a protein exhibiting CSGalNAcT-1 activity, the gene encoding CSGalNAcT-1 may be a nucleic acid molecule including a nucleotide sequence identical to that defined by SEQ ID NO: 3, except that one or more nucleotide(s) have been substituted, deleted, inserted, or transposed. The number of such nucleotides is preferably 2 to 20, more preferably 2 to 10, particularly preferably 2 to 5.

The gene encoding CSGalNAcT-1 also includes a nucleic acid which has a high sequence identity (including as preferable examples, 75-100%, 80-100%, or 90-100% sequence identity, or 91%, 92%, 93%, 94%, 95%, 96%, 97%, 98%, 99%, 99.5%, or 99.9% sequence identity; higher sequence identities are more preferable among the above examples) to a nucleotide sequence defined by SEQ ID NO: 3.

The aforementioned homologue genes include naturally occurring species-dependent variants and variants produced through treatment such as UV irradiation or treatment with a variation-inducing agent. The gene encoding CSGalNAcT-1 may be a gene derived from a non-human organism. However, when the product is employed as a drug for human use, a human-derived gene is preferred. Thus, the gene encoding CSGalNAcT-1 may be a nucleic acid molecule including a nucleotide sequence encoding an amino acid sequence defined by SEQ ID NO: 4.

As used herein, the term "CSGalNAcT-1 activity" refers to activity of transferring an N-acetylgalactosamine residue from an N-acetylgalactosamine donor to a non-reducing end D-glucuronate residue of an N-acetylgalactosamine acceptor substrate containing a sugar chain represented by formula: GlcUA-Gal-Gal-Xyl (wherein GlcUA represents a D-glucuronate residue, Gal represents a D-galactose residue, Xyl represents a D-xylose residue, and "-" represents a glycosidic linkage).

The CSGalNAcT-1 activity may be determined through a method disclosed in J. Biol. Chem. 2002 Mar. 15; 277 (11): 8841-6.

When the aforementioned gene encoding chondroitin sulfate glucuronyltransferase and/or gene encoding chondroitin sulfate N-acetylgalactosaminyltransferase-1 is formulated as an active ingredient of the chondroitin sulfate synthesis promoter, the gene(s) may be formulated through a method for preparing a genetic drug generally employed in a genetic therapy.

Preferably, the gene encoding chondroitin sulfate glucuronyltransferase and a gene encoding chondroitin sulfate N-acetylgalactosaminyltransferase-1 are incorporated into an expression vector.

In the above expression vector, regions relating to the gene expression (promoter region, enhancer region, operator region, etc.) may be appropriately arranged so that the gene is expressed. For example, the expression vector may include vectors such as pcDNA3.1 (+), pCDM8, or pcDNA3 expression vector (product of Invitrogen).

The gene can be incorporated into an expression vector using techniques well known to the skilled artisan.

Preferably, the gene encoding chondroitin sulfate glucuronyltransferase and a gene encoding chondroitin sulfate N-acetylgalactosaminyltransferase-1 are incorporated into a host cell.

Suitable host cells include a wide variety of prokaryotic and eukaryotic host cells. For example, the polypeptides of the invention may be expressed in bacterial cells such as *E. coli*, insect cells (using baculovirus), yeast cells, fungal cells, insect cells, and plant or animal cells, in particular mammalian cells. Other suitable host cells can be found in Goeddel (1991) Gene Expression Technology Methods in Enzymology 185, Academic Press, San Diego, Calif. A method for incorporating the gene into the host cell is not particularly limited. Methods for introducing exogenous genetic material into host cells are well known to the skilled artisan, and the gene can be incorporated into the host cell using such techniques. Preferably, a gene which is incorporated into an expression vector may be incorporated into the host cell.

Specific examples of methods for incorporating the gene into the vector, and introducing genes to target tissue are shown below.

For example, the CSGlcAT gene or the CSGalNAcT-1 gene is ligated to a promoter which can be expressed in target tissue, to thereby produce a gene construct, and the gene construct per se or a vector containing the gene construct is introduced into target tissue. Although the promoter may be a constitutionally expressed promoter such as a CMV promoter, the promoter is preferably a tissue-specific promoter. Examples of the target tissue include articular cartilage and intervertebral disk tissue. In the case where the target is chondrocytes or vertebral pulp cells, a promoter which functions in chondrocytes or vertebral pulp cells; e.g., a collagen gene promoter, may be employed. Examples of employable vectors include virus vectors such as an adenovirus vector and a retrovirus vector, and plasmid vectors. In one possible mode, a CSGlcAT gene or a CSGalNAcT-1 gene is ligated to a type-2 collagen promoter, to thereby form a gene construct, and the gene construct is introduced to an adenovirus vector. Through incorporation of the product, the gene of the present invention can be introduced to target tissue (e.g., intervertebral disk tissue).

Other than the above gene construct, a nucleotide sequence defined by SEQ ID NO: 1 or a nucleotide sequence defined by SEQ ID NO: 3 may be ligated with a tag sequence generally employed in a recombination technique, to thereby form a gene construct. For example, a gene construct in which a V5 epitope tag is ligated to the nucleotide sequence may be produced. Of course, a gene construct in which both of a promoter and a tag sequence are ligated to the nucleotide sequence may be produced. Through employment of a general recombination technique, a gene construct in which a different sequence is ligated to the nucleotide sequence is expressed, whereby a fusion protein can be expressed.

The gene construct containing a CSGlcAT gene or a CSGalNAcT-1 gene or the vector containing the gene construct may be introduced in combination with a pharmacologically acceptable carrier. Examples of the pharmacologically acceptable carrier include physiological saline, a stabilizer, a nuclease inhibitor, and a complexing agent such as EDTA. Alternatively, the gene construct containing a CSGlcAT gene or a CSGalNAcT-1 or the vector containing the gene construct may be introduced in the form of a complex with ribosome. Still alternatively, cells such as chondrocytes transfected with the gene construct containing a CSGlcAT gene or a CSGalNAcT-1 gene or the vector containing the gene construct may serve as a chondroitin sulfate synthesis promoter and be introduced to tissue such as cartilage.

The CSGlcAT gene or the CSGalNAcT-1 gene of the present invention may be applied to a genetic therapy employing a gene gun (e.g., a gene gun or a particle gun). The gene gun is a device for introducing an extraneous gene into a cell or tissue preferably through implanting a carrier harboring an extraneous gene or a composition containing an extraneous gene by pressure or other means. In other words, the present invention may employ a gene gun for introducing the gene of the present invention through implanting a gene introduction carrier harboring the gene of the present invention into cartilage, a vertebral pulp cell, etc., which gene gun has a tube for accelerating a gas such as helium, a mechanism for holding the gene introduction carrier harboring the gene, and other members and which has dimensions suitable for introduction of the gene to the target tissue. The carrier which is employed in the gene gun method preferably has little affect on cells and tissue. Although other carriers can be used, one preferred example of a carrier is gold particles.

In one possible mode, the CSGlcAT gene or the CSGalNAcT-1 gene of the invention is chemically or physically adsorbed onto spermidine-coated gold particles, to thereby provide a gene-harboring carrier, and the carrier is implanted into the target tissue such as cartilage or cells by means of a gene gun, whereby the gene of the present invention is introduced to the target tissue or cells.

Although no particular limitation is imposed on the administration method, the genetic drug is preferably administered topically to the target tissue. The dose of the genetic drug may be appropriately adjusted in accordance with the expression efficiency of a nucleic acid molecule and gravity of the target disease.

In a second embodiment of the present invention, the chondroitin sulfate synthesis promoter contains, as an active ingredient, a chondroitin sulfate glucuronyltransferase or chondroitin sulfate N-acetylgalactosaminyltransferase-1.

Examples of the CSGlcAT protein include human CSGlcAT having an amino acid sequence defined by SEQ ID NO: 2. The protein may be obtained through extraction from an organism, followed by purification, or through a genetic engineering technique. For example, the protein is obtained through introducing a gene having a nucleotide sequence as defined by SEQ ID NO: 1 into *E. coli*, animal cells, or a non-human transgenic animal, to thereby express a recombinant protein, followed by purification. Examples of the vector for introducing the gene into *E. coli* include pET vector (product of Novagen) and pGEX vector (product of Amersham Pharmacia), and examples of the vector for introducing the gene into animal cells include pcDNA vector (product of Invitrogen).

The CSGlcAT protein is believed to readily undergo variation such as substitution of amino acids depending on species. However, if an amino acid is substituted by another amino acid having similar characteristics (conservative substitution) or a certain amino acid not essential for exerting transfer activity is deleted, CSGlcAT activity is believed not to be affected. Therefore, so long as the nucleic acid molecule encodes a protein exhibiting CSGlcAT activity, in an amino acid sequence defined by SEQ ID NO: 2, one or more amino acid(s) may be substituted, deleted, inserted, or transposed. The number of such nucleotides is preferably 2 to 20, more preferably 2 to 10, particularly preferably 2 to 5.

The CSGlcAT protein may be derived from a non-human organism. However, when the product is employed as a drug for human use, a human-derived protein (this includes human-derived protein obtained by means of genetic engineering using a human-derived gene, for example) is preferred.

Examples of the CSGalNAcT-1 protein include human CSGalNAcT-1 protein having an amino acid sequence defined by SEQ ID NO: 4. The protein may be obtained through extraction from an organism, followed by purification, or through a genetic engineering method. For example, the protein is obtained through introducing a gene having a nucleotide sequence as defined by SEQ ID NO: 3 into *E. coli*, animal cells, or a non-human transgenic animal, to thereby express a recombinant protein, followed by purification.

The CSGalNAcT-1 protein is believed to readily undergo variation such as substitution of amino acids depending on species. However, if an amino acid is substituted by another amino acid having similar characteristics (conservative substitution) or a certain amino acid not essential for exerting transfer activity is depleted, CSGalNAcT-1 activity is believed not to be affected. Therefore, so long as the nucleic acid molecule encodes a protein exhibiting CSGalNAcT-1 activity, in an amino acid sequence defined by SEQ ID NO: 4, one or more amino acid(s) may be substituted, deleted, inserted, or transposed. The number of such nucleotides is preferably 2 to 20, more preferably 2 to 10, particularly preferably 2 to 5.

The CSGalNAcT-1 protein may be derived from a non-human organism. However, when the product is employed as a drug for human use, a human-derived protein (this includes human-derived protein obtained by means of genetic engineering using a human-derived gene, for example) is preferred.

It is generally known that enzymes exist which have glycochains. Also, it is possible to express enzymes which have glycochains through genetic engineering. A chondroitin sulfate glucuronyltransferase or chondroitin sulfate N-acetylgalactosaminyltransferase-1 in the present invention may have parts such as glycochains in addition to their protein.

The CSGlcAT protein or the CSGalNAcT-1 protein per se may be employed as a chondroitin sulfate synthesis promoter. Alternatively, the above protein may be blended with a pharmacologically acceptable carrier, and the mixture may be employed as the synthesis promoter. Examples of the carrier include a vehicle, a stabilizer, a tonicity agent, a surfactant, and a buffer. No particular limitation is imposed on the drug form of CSGlcAT protein or CSGalNAcT-1 protein, and examples include injection, ointment, cream, fomentation, and liniment.

Although no particular limitation is imposed on the administration method, the protein drug is preferably administered topically to the target tissue. The dose of the protein drug may be appropriately adjusted in response to gravity of the target disease or other factors.

No particular limitation is imposed on the diseases and disorders to which the chondroitin sulfate synthesis promoter of the present invention is applied, so long as they can be treated by increasing the chondroitin sulfate level. However, the chondroitin sulfate synthesis promoter is preferably employed for improving functions of articular cartilage and intervertebral disk tissue. For example, the chondroitin sulfate synthesis promoter may serve as a treatment agent for a decrease in cartilage; articular diseases such as osteoarthritis and traumatic articular disorders; or discopathy such as intervertebral disk degradation or herniated disk, which are caused by aging, disease, injury, etc.

The present inventors have elucidated that each of CSGlcAT and CSGalNAcT-1 promotes synthesis of chondroitin sulfate in chondroid cells. Therefore, a compound which increases expression of a CSGlcAT gene or a CSGalNAcT-1 gene may be a candidate for a low-molecular drug for promoting synthesis chondroitin sulfate. In one screening procedure for the chondroitin sulfate synthesis promoter, each test compound is added to cartilage culture cells, and the protein level or mRNA level in relation to CSGlcAT or CSGalNAcT-1 is determined. Among test compounds, a compound which increases the protein level or mRNA level in relation to CSGlcAT or CSGalNAcT-1 is selected.

Alternatively, a CSGlcAT gene and/or a CSGalNAcT-1 gene is expressed in vitro in cultured chondrocytes, to thereby form cells exhibiting enhanced chondroitin sulfate synthesis performance, which serve as transplant chondrocytes. The cultured chondrocytes are preferably human-derived. By use of a virus vector or a plasmid vector containing a CSGlcAT gene and/or a CSGalNAcT-1 gene, these genes are expressed in cultured chondrocytes, and promotion of chondroitin sulfate synthesis is confirmed. Thereafter, the thus-gene-introduced cultured chondrocytes are transplanted into a disordered site.

Further the present invention provides a method for promoting chondroitin sulfate synthesis in a living subject wherein the living subject includes a joint, a cartilage, an intervertebral disc or a cell (including a chondrocyte), the method comprising the steps of:
    providing a gene comprising a gene encoding chondroitin sulfate glucuronyltransferase or a gene encoding chondroitin sulfate N-acetylgalactosaminyltransferase-1; and
    introducing the gene into the living subject.

Preferably the step of introducing the gene into the living subject is performed with a gene gun or via injection. Please refer to the above said explanations about the gene gun or gene therapy.

Preferably a living subject is a living subject derived from mammal such as human, domestic animal (including for example, a horse, cattle, and pig), or pet (including for example, dog and cat), for example.

Further the present invention provides a method for promoting a chondroitin sulfate synthesis in a living subject wherein the living subject includes a joint, a cartilage, an intervertebral disc or a cell (including a chondrocyte), the method comprising the steps of:
    providing a chondroitin sulfate glucuronyltransferase or chondroitin sulfate N-acetylgalactosaminyltransferase-1; and
    introducing a chondroitin sulfate glucuronyltransferase or chondroitin sulfate N-acetylgalactosaminyltransferase-1 into the living subject.

Preferably a living subject is a living subject derived from mammal such as human, domestic animal (including for example, a horse, cattle, and pig), or pet (including for example, dog and cat), for example.

Preferably the step of introducing a chondroitin sulfate glucuronyltransferase or chondroitin sulfate N-acetylgalactosaminyltransferase-1 into the living subject can be performed via injection, for example.

Further the present invention provides a method for treating an articular disease or discopathy, the method comprising the steps of:
    applying a therapeutically effective amount of an active ingredient comprising a chondroitin sulfate glucuronyltransferase, a gene encoding chondroitin sulfate glucuronyltransferase, a chondroitin sulfate N-acetylgalactosaminyltransferase-1, or a gene encoding a chondroitin sulfate N-acetylgalactosaminyltransferase-1 with the affected joint or intervertebral disc; and promoting a chondroitin sulfate synthesis in the affected joint or intervertebral disc.

The method to apply the active ingredient with the affected joint or intervertebral disc is not particularly limited. When the active ingredient is selected from a gene encoding chondroitin sulfate glucuronyltransferase and a gene encoding a chondroitin sulfate N-acetylgalactosaminyltransferase-1, gene gun or injection can be used preferably. When the active ingredient is selected from a chondroitin sulfate glucuronyltransferase and a chondroitin sulfate N-acetylgalactosaminyltransferase-1, injection can be used preferably.

A therapeutically effective amount is a concentration or amount of the active ingredient which is effective for achieving a therapeutic effect. This amount may also be determined empirically.

EXAMPLES

The present invention will next be described in detail by way of examples, which should not be construed as limiting the invention thereto.

Example 1

Expression of Chondroitin Sulfate Glycosyltransferase in Cartilage

Humeri were obtained from mouse E16.5 embryos, and in situ hybridization was performed in order to confirm expression of chondroitin sulfate glycosyltransferase in cartilage.

Digoxigenin (DIG)-11-UTP-labeled single-strand antisense RNA probes corresponding to mouse CSS-1, CSS-2, CSS-3, CSGlcAT, CSGalNAcT-1, CSGalNAcT-2, aggrecan, versican, and type-10 collagen α1 chain (Col10a1) were prepared by use of a DIG RNA labeling kit (product of Boehringer Mannheim) according to the manufacturer's instructions. Each humerus sample was collected from a mouse E16.5 embryo, and a paraffin section thereof was prepared. After removal of paraffin, the section was fixed with 4% paraformaldehyde for 10 minutes and treated with 20-ng/mL protein kinase K (product of Roche) at 37° C. for 7 minutes. Another fixation was performed with 4% paraformaldehyde for 10 minutes, followed by treating with 0.2-mol/L hydrochloric acid for 10 minutes and 0.25-mol/L acetic anhydride/ 0.1-mol/L triethylamine (TEA) for 10 minutes. The thustreated section was dehydrated with ethanol and dried under air. The dried section was hybridized with 1.0-μg/mL RNA probe at 50° C. for 20 hours. The product was washed with 2×SSC (buffer: 0.3-mol/L sodium citrate and 3-mol/L sodium chloride)/50% formamide. Subsequently, the washed product was treated with 20 μg/mL RNaseA/TNE buffer (10-mmol/L Tris-HCl (pH: 8.0), 0.5-mol/L sodium chloride, and 1-mmol/L dihydrogen sodium ethylenediaminetetraacetate (EDTA)) at 37° C. for 20 minutes, and washed with 2×SSC at 50° C. for 10 minutes and a 20×SSC at 50° C. for 20 minutes. The product was blocked with a 1.5% blocking reagent (product of Applied Biosystems) at 37° C. for one hour, reacted with a 1:500 anti-DIG antibody (product of Roche) at 37° C. for one hour, and colored with an NBT/BIP (nitroblue tetrazolium hydrochloride/bromochloroindolylphosphoric acid, product of Roche) at room temperature for 56 hours. Hematoxylin staining and alcian blue staining were also performed.

The results are shown in FIG. 1.

Among six chondroitin sulfate glycosyltransferases, considerable expression of mRNA was confirmed in cartilage for four glycosyltransferases: CSS-1, CSS-2, CSGlcAT, and CSGalNAcT-1. CSS-3 and CSGalNAcT-2 were not found to be expressed. In articular cartilage covering the articular plate and growth cartilage, the above four glycosyltransferases were colocalized with core proteins of aggrecan and versican, confirming expression of the four glycosyltransferases.

Example 2

Expression Patterns of Chondroitin Sulfate Glycosyltransferases During Chondrocyte Differentiation Chondrogenic ATDC5 cells were cultured in Dulbecco's modified Eagle medium (DMEM)/F-12 medium containing 5% fetal bovine serum (FBS), penicillin and streptomycin. In order to induce differentiation of chondrocytes, the cells at confluency were treated with 10-μg/mL bovine insulin, 10-μg/mL human transferrin, and $3\times10^{-8}$-mol/L sodium selenite.

On days 1, 3, 5, 7, 14, and 21 after induction of differentiation (day 0: at about 80% confluency (growing phase) before induction of differentiation), the expression amount of mRNA (a gene transcription product) corresponding to mouse CSS-1, CSS-2, CSS-3, CSGlcAT, CSGalNAcT-1, CSGalNAcT-2, or aggrecan was determined through real time RT-PCR.

mRNA was extracted by use of Micro-FastTrack (product of Invitrogen), and cDNA was reverse transcribed therefrom by use of SuperScript First-Strand (product of Invitrogen). The primers and fluorescence-labeled probes corresponding to the genes are shown in Table 1, and were designed by use of Primer Express 1.0 software.

TABLE 1

| Gene (GenBank Accession No.) | | |
|---|---|---|
| aggrecan derived from mouse (NM_007424) | Forward primer | ctgcccttgccccgtaa (SEQ ID NO: 5) |
| | Reverse primer | gacaggtcaaagatgggctttg (SEQ ID NO: 6) |
| | Probe | ccctgggcagcgtgatcctcac (SEQ ID NO: 7) |
| CSS-1 derived from mouse (XM_194358) | Forward primer | ctggacctgctgctcctgtat (SEQ ID NO: 8) |
| | Reverse primer | tcttcagggaattggacaggaa (SEQ ID NO: 9) |
| | Probe | cagcagaccttcagcaagatgcagtttgt (SEQ ID NO: 10) |

TABLE 1-continued

| Gene (GenBank Accession No.) | | |
|---|---|---|
| CSS-2 derived from mouse (XM_129886) | Forward primer | gggcttggagtcttgctctct (SEQ ID NO: 11) |
| | Reverse primer | ggcgagcactgacgatgtc (SEQ ID NO: 12) |
| | Probe | acagcaactgcgcccccacct (SEQ ID NO: 13) |
| CSS-3 derived from mouse (XM_128873) | Forward primer | ggaaactgggttttggagagacta (SEQ ID NO: 14) |
| | Reverse primer | ccgtaagccagataggatgacttta (SEQ ID NO: 15) |
| | Probe | acggaatccaatgcatttacaaaaacgatc (SEQ ID NO: 16) |
| CSGlcAT derived from mouse (NM_133913) | Forward primer | tggccgtcgcggttaa (SEQ ID NO: 17) |
| | Reverse primer | tccatgagacaccacctgcat (SEQ ID NO: 18) |
| | Probe | cgtacagtagcacatcacttccctcggttact (SEQ ID NO: 19) |
| CSGalNAcT-1 derived from mouse (BC057630) | Forward primer | tgagctggtagaagccatcga (SEQ ID NO: 20) |
| | Reverse primer | gttcggtaaatcccttctatgaagtc (SEQ ID NO: 21) |
| | Probe | cggccctggagagtctaaacagccct (SEQ ID NO: 22) |
| CSGalNAcT-2 derived from mouse (NM_030165) | Forward primer | gctgagccaggtaaaaaggtgtt (SEQ ID NO: 23) |
| | Reverse primer | aaaccagagtcctttttatgaacca (SEQ ID NO: 24) |
| | Probe | caggacgtgccgcccctg (SEQ ID NO: 25) |

PCR was performed by use of 5-μL cDNA, 25-μL TaqMan Universal PCR Master Mix (product of Applied Biosystems), 100-nmol/L probe, and 100-nmol/L primer (total 50 μL), and determination was performed on a 96-well plate by means of an ABI Prism 7700 (product of Applied Biosystems).

The aforementioned mRNA levels were standardized by an amount of a gene transcription product (mRNA level) of glycerinaldehyde triphosphate dehydroganase (GAPDH) determined through the same method. The thus-standardized mRNA expression levels were plotted as fold numbers against day 0 (before induction of differentiation (FIG. 2)).

Example 3

Expression Patterns of Chondroitin Sulfate Glycosyltransferases During Chondrocyte Differentiation Chondrogenic N1511 cells were cultured in a minimum essential medium α (α-MEM medium) supplemented with 10% FBS, penicillin, and streptomycin at 37° C. under 5% $CO_2$. The cells at confluency were treated with $1 \times 10^{-6}$-mol/L dexamethasone solution and $1 \times 10^{-7}$-mol/L rat parathyroid hormone (PTH) solution, to thereby induce differentiation. In a manner similar to that of Example 2, on days 1, 3, 5, 7, 14, and 21 after induction of differentiation (day 0: at about 80% confluency (growing phase) before induction of differentiation), the level of mRNA (a gene transcription product) corresponding to CSS-1, CSS-2, CSS-3, CSGlcAT, CSGalNAcT-1, CSGalNAcT-2, or aggrecan was determined. In a manner similarly to that of Example 2, the aforementioned mRNA levels were standardized by an mRNA level of GAPDH. The thus-standardized mRNA expression levels were plotted as fold numbers with respect to those at day 0 (before induction of differentiation) (FIG. 3).

Figure 2:
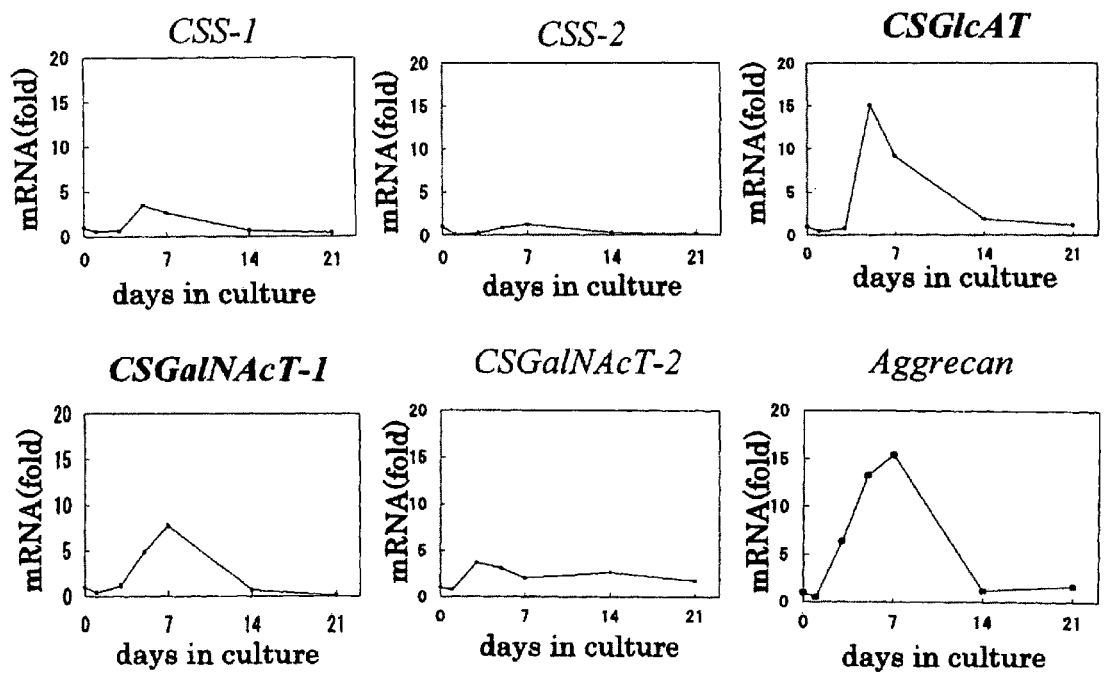
FIG. 2 shows RT-PCR results representing expression patterns of chondroitin sulfate glycosyltransferases during differentiation of ATDC5 cells.
Figure 3:
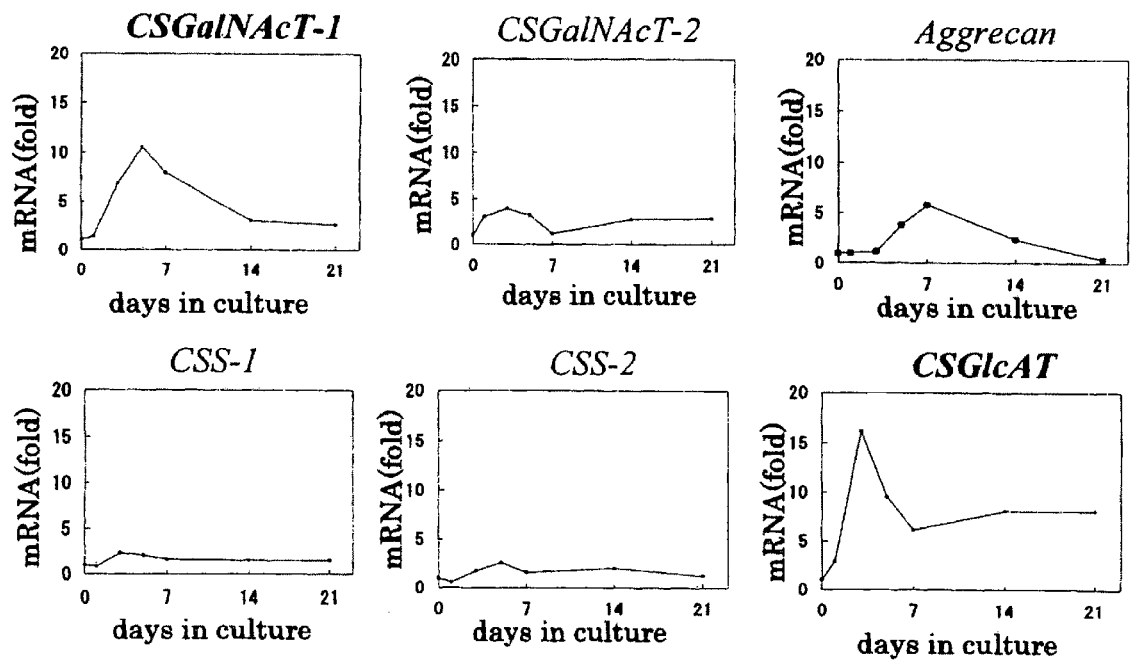
FIG. 3 shows RT-PCR results representing expression patterns of chondroitin sulfate glycosyltransferases during differentiation of N1511 cells.

As is clear from FIGS. 2 and 3, in both the case where differentiation of ATDC5 cells was induced and the case where differentiation of N1511 cells was induced, CSGlcAT transcriptional level and CSGalNAcT-1 transcriptional level increased remarkably, as compared with other enzymes. Meanwhile, it has already been known that aggrecan synthesis is promoted in chondrogenic cells such as ATDC5 cells and N1511 cells during an induced differentiation step. For example, in the case of ATDC5 cells, the aggrecan core protein transcription product (mRNA) level reaches the peak 7 to 10 days after induction of differentiation. In the above experiments, the aggrecan transcriptional level reached the peak approximately at day 7, indicating that transcriptional levels of CSGlcAT and CSGalNAcT-1 are correlated to the change in gene transcriptional level with respect to aggrecan core protein. Therefore, CSGlcAT and CSGalNAcT-1 are believed to be involved in chondroitin sulfate chain synthesis in cartilage. Note that a CSS-3 transcription product (mRNA) was not detected over the period of the experiment.

Example 4

Expression Patterns of Chondroitin Sulfate Glycosyltransferases in Mouse Embryonic Fibroblasts Mouse embryonic fibroblasts (MEFs, product of BD Bioscience) were cultured in a DMEM medium supplemented with 10% FBS, penicillin, and streptomycin at 37° C. under 5% $CO_2$.

At a growing phase (about 80% confluency) and one week after confluency, the level of mRNA (a gene transcription product) corresponding to CSS-1, CSS-2, CSGlcAT, CSGalNAcT-1, CSGalNAcT-2, or aggrecan was determined through the same method as employed in Example 2. Similar to Example 2, the mRNA levels were standardized by an mRNA level of GAPDH.

Figure 4:
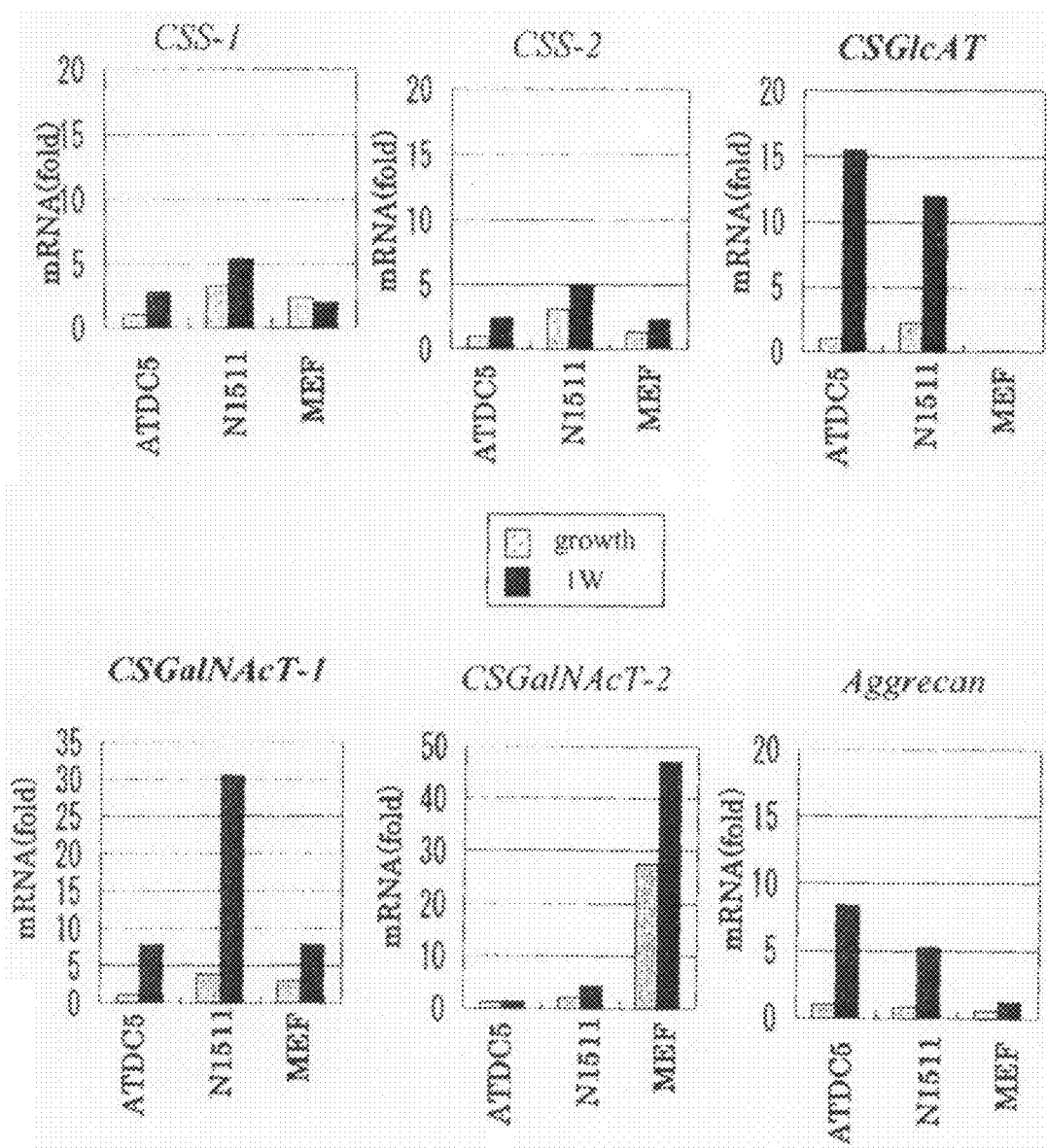
FIG. 4 shows expression levels of chondroitin sulfate glycosyltransferases in ATDC5 cells, N1511 cells, and mouse embryonic fibroblasts (MEFs)

Expression levels (mRNA levels) of the genes at the growing phase (day 0) before induction of differentiation and at one week after induction of differentiation in Examples 2 and 3, and expression levels (mRNA levels) of the genes at the growing phase and at one week after confluency in Example 4 were plotted as fold numbers with respect to those at the growing phase of ATDC5 cells determined in Example 2 (FIG. 4).

mRNA expression levels of CSGlcAT, CSGalNAcT-1, and aggrecan were remarkably increased one week after induction of differentiation in chondrogenic cells such as ATDC5 cells and N1511 cells, and the increase was found to be correlated with increase in aggrecan. In contrast, mRNA expression level of CSGlcAT was virtually unobserved in mouse embryonic fibroblasts (MEFs), which are not differentiated to chondrocytes, and mRNA expression level of CSGalNAcT-1 was not considerably changed as compared with chondrogenic cells.

In Examples 2, 3, and 4, expression of CSGlcAT and CSGalNAcT-1 correlated highly with chondrocyte differentiation in chondrogenic cells.

Similar to Example 1, mRNA expression level of CSGalNAcT-2 was greater in fibroblasts and was virtually unobserved in chondrogenic cells.

Example 5

Establishment of CSGlcAT-Transfected Cells and CSGalNAcT-1-Transfected Cells

Rat chondrosarcoma cells (LTC cells) were transfected with human CSGlcAT and CSGalNAcT-1 expression vectors, respectively, followed by culturing. The transfected cells were selected by use of 1-mg/mL G418 disulfate (product of Nacalai Tesque).

Each of the above expression vectors was produced by incorporating cDNA of human CSGlcAT or cDNA of CSGalNAcT-1 into a pcDNA3.1 (+) vector (product of Invitrogen) (the expression vectors were donated by Dr. Goto of Advanced Industrial Science and Technology, Research Center for Glycoscience).

Rat chondrosarcoma cells (LTC cells) were cultured in a DMEM medium supplemented with 10% FBS, penicillin, and streptomycin at 37° C. under 5% CO2. Each expression vector was cut with a restriction enzyme PvuI (product of New England Biolabs) and linearized, and the LTC cells were transfected with the vector using FuGENE6 (product of Roche) in accordance with the manufacturer's instructions. On the day following transfection, 1-mg/mL G418 was added to the above culture, and culturing was further performed for 10 days, whereby transfected cells were selected. As a control, Mock-transfected cells were established in a similar manner through transfection with pcDNA3.1 (+) (product of Invitrogen) instead of the above enzymes.

Example 6

Analysis of Transfected Cells

The transfected cells established in Example 5 were analyzed as follows.

(1) Determination of Expression Levels of Enzymes:

CSGlcAT, CSGalNAcT-1, and Mock were analyzed in terms of expression levels of the corresponding exogenous enzymes (human-derived) and endogenous enzymes (rat-derived) according to the method employed in Example 2 through real time RT-PCR. The primers and fluorescence-labeled probes corresponding to the genes are shown in Table 2, and were designed by use of Primer Express 1.0 software.

TABLE 2

| Gene (GenBank Accession No.) | | |
|---|---|---|
| CSGlcAT derived from human (AB037823) | Forward primer | ctagaccaaagtgatgaagacttcaaac (SEQ ID NO: 26) |
| | Reverse primer | tgtaccgagtcctgagcaccTt (SEQ ID NO: 27) |
| | Probe | ctacagggaccccaacaagccctacaag (SEQ ID NO: 28) |
| CSGalNAcT-1 derived from human (AB08 1516) | Forward primer | agcagcaccgcaactacgt (SEQ ID NO: 29) |
| | Reverse primer | ctggcttggtactgcccatt (SEQ ID NO: 30) |
| | Probe | ctgaagcggcagatcgcacagct (SEQ ID NO: 31) |
| CSGlcAT derived from rat (XM_216063) | Forward primer | tggccgtcgctgttaa (SEQ ID NO: 32) |
| | Reverse primer | tccatgagacaccacctgcat (SEQ ID NO: 33) |
| | Probe | cgtacagtggcacatcacttccctcggttact (SEQ ID NO: 34) |
| CSGalNAcT-1 derived from rat (XM_224757) | Forward primer | tgagctagtggaagctatcga (SEQ ID NO: 35) |
| | Reverse primer | gttcggtagatcccttctatgaagtc (SEQ ID NO: 36) |
| | Probe | cagccctggagagtctaaacagccct (SEQ ID NO: 37) |

Figure 5:
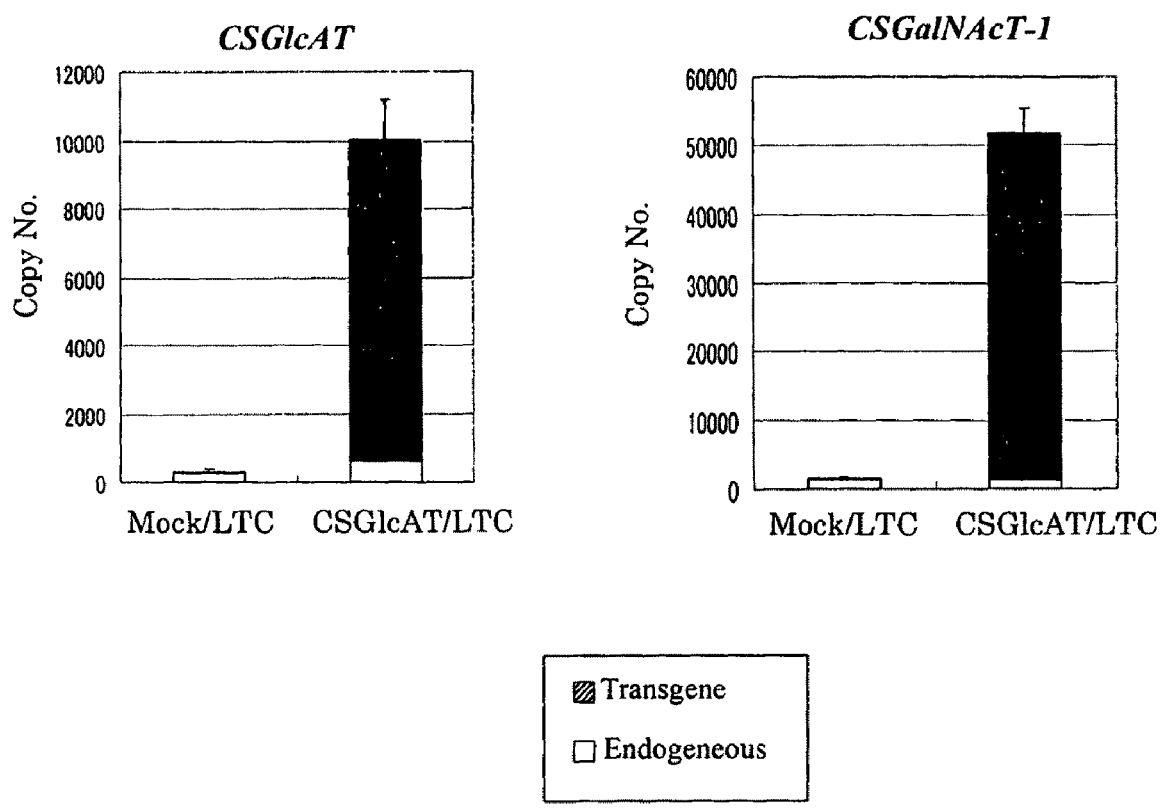
FIG. 5 shows expression levels of CSGlcAT and CSGalNAcT-1 in transfected cells.

Reference to the respective expression vectors as controls, copy numbers (transcriptional levels) of human CSGlcAT and CSGalNAcT-1 and rat CSGlcAT and CSGalNAcT-1 are shown in FIG. 5.

Figure 6:
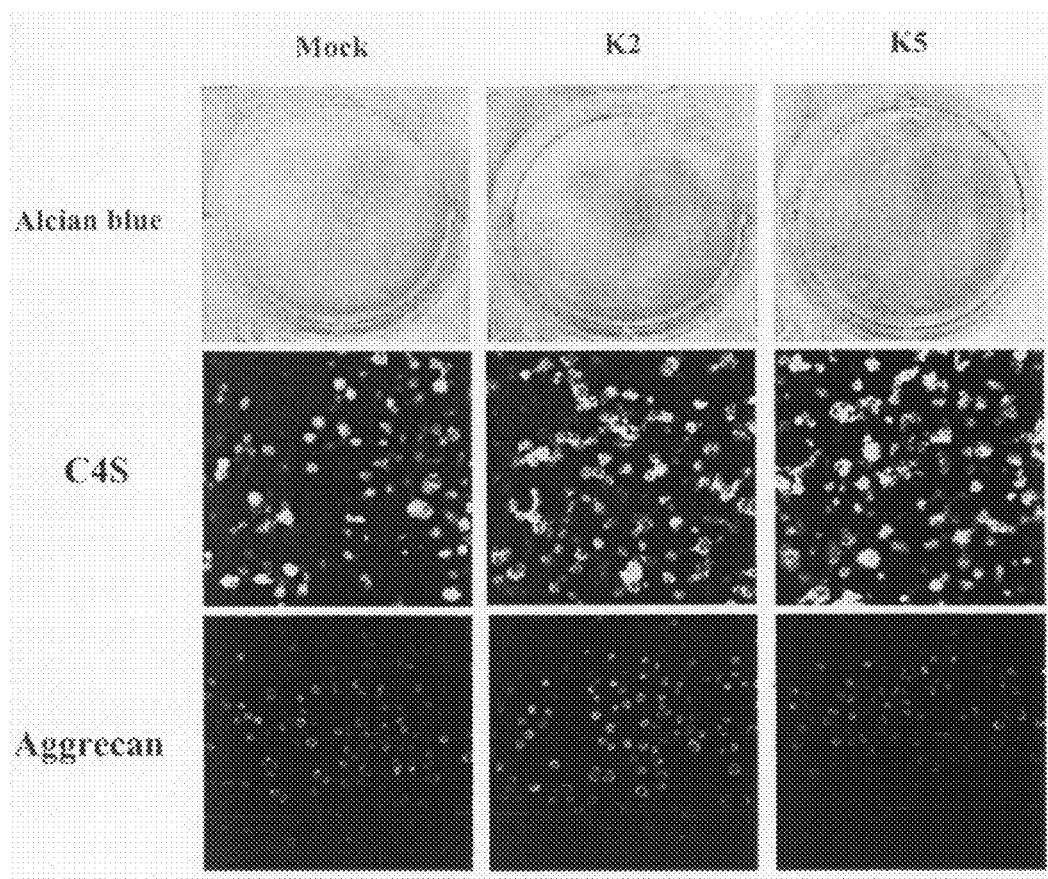
FIG. 6 shows results of Alcian Blue staining and immunostaining (employing anti-chondroitin 4-sulfate (C4S) antibody or anti-aggrecan antibody) of control (Mock) and sample of transfected cells (photographs)

(2) Alcian Blue Staining and Immunostaining:

In Alcian Blue staining, each transfected cell was seeded onto a DMEM medium supplemented with 10% FBS, penicillin, and streptomycin placed in a 6-well plate, followed by culturing at 37° C. under 5% $CO_2$. One day after, the culture was fixed in an 80%-confluency state with 4% paraformaldehyde and treated for 30 minutes with 0.1% Alcian Blue dissolved in 0.1-mol/L hydrochloric acid (FIG. 6, upper).

Immunostaining was performed by use of a mouse monoclonal antibody reacting with chondroitin-4-sulfate (C4S) (Ab-Chondroitin-4-Sulfate/chicken (LY111), product of SEIKAGAKU CORPORATION) and a rabbit polyclonal antibody against aggrecan (FIG. 6, lower) (the rabbit polyclonal antibody against aggrecan was donated by Dr. Yada of Institute for Molecular Science of Medicine, Aichi Medical University).

(3) Determination of Chondroitin Sulfate Synthesis Activity:

LTC cells transfected with a CSGlcAT gene and those transfected with a CSGalNAcT-1 gene were cultured in cell culture dishes (3003, product of Falcon) containing a DMEM medium supplemented with 10% FBS, penicillin, and streptomycin, at 37° C. under 5% CO2. On the following day, 100-μCi/mL$^{35}$ S sulfate was added to each culture, followed by culturing for 24 hours, so as to label the cells. Subsequently, cells and a culture medium were separately collected and extracted with 0.1-mol/L sodium hydride solution at 4° C. for 16 hours. Subsequently, the system was neutralized with 4-mol/L acetic acid. Under 20-mmol/L Tris-HCl (pH: 8.0) buffered conditions, 5-μL protein kinase K (20 mg/mL, product of Roche) was added to the system, followed by treatment at 37° C. for 12 hours. Through heating to 100° C., protein kinase K was inactivated. Then, 10-μL DNaseI (10 mg/mL, product of Boehringer Mannheim) and 10-μL RNaseA (10 mg/mL, product of Wako) were added to the above system, followed by treatment at 37° C. for two hours. Glycosaminoglycan (GAG) chains were collected from the reaction mixture. The thus-collected GAG chains were applied to a DEAE-Sepharose column. The column was washed with a 0.2-mol/L aqueous sodium chloride solution, and GAG fractions were eluted with an aqueous 2-mol/L sodium chloride solution. The thus-obtained GAG was precipitated with a 1.3% aqueous potassium acetate solution and 95% ethanol, and the thus-obtained precipitate was suspended in a buffer (50-mmol/L Tris-HCl (pH: 7.5)-0.2-mol/L sodium chloride). The GAG suspension was divided into three portions, and the portions were treated with a heparitinase mixture containing heparitinase I, heparitinase II, and heparinase (all enzymes are products of SEIKAGAKU CORPORATION); treated with a chondroitinase ABC (product of SEIKAGAKU CORPORATION); and non-treated, respectively. Subsequently, each of the thus-treated GAG samples was applied to a Superrose 6 (product of Amersham Biosciences) column which had been equilibrated with an aqueous solution (50-mmol/L Tris-HCl (pH: 7.5)-0.2-mol/L sodium chloride), and eluted with the aqueous solution (50-mmol/L Tris-HCl (pH: 7.5)-0.2-mol/L sodium chloride), whereby 0.5-mL fractions were collected. Radioactivity of labeled GAG contained in each fraction was measured by means of a liquid scintillation counter, and an elution curve was obtained through the data of scintillation counting (FIG. 7, lower).

Figure 7:
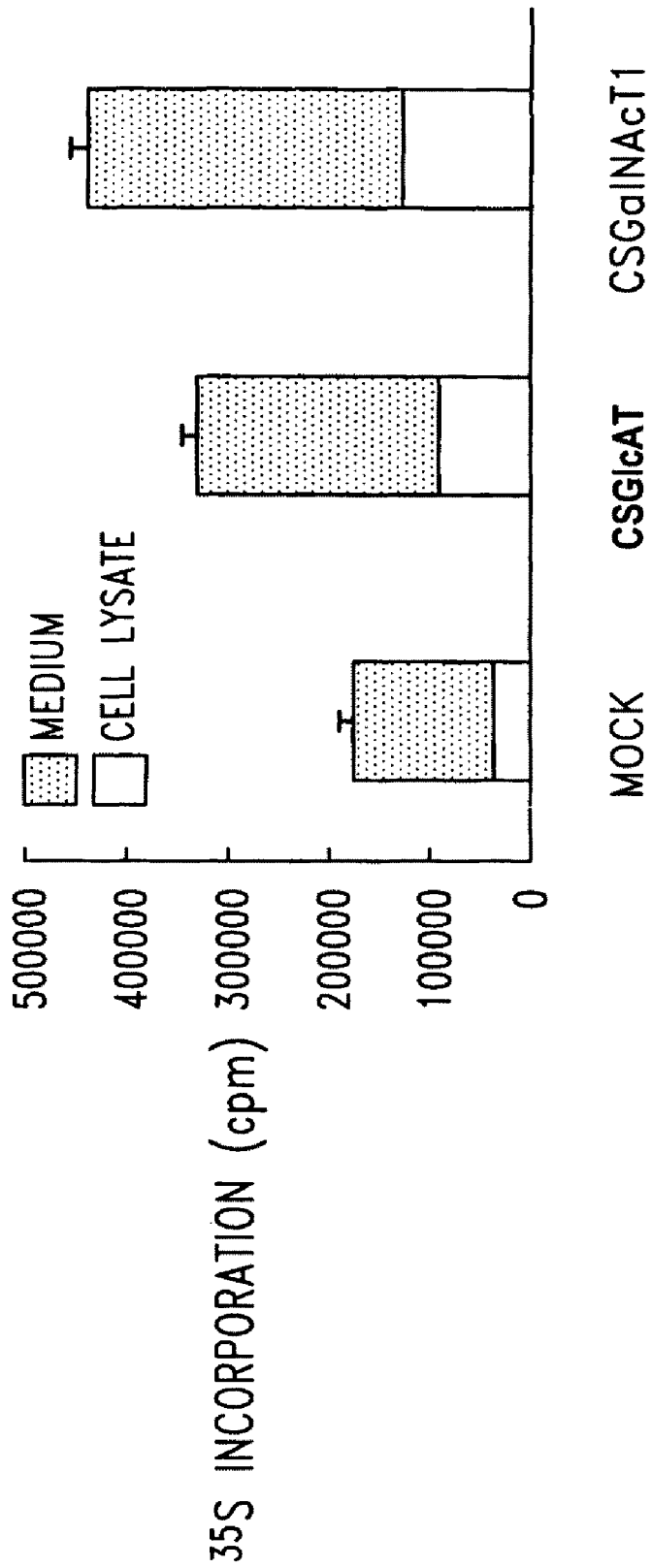
FIG. 7 shows chondroitin sulfate synthesis activities of control (Mock) and sample of transfected cells as determined by labeled chondroitin sulfate levels in culture media and cell lysates, wherein "-" denotes no treatment, "HSase" denotes heparitinase mixture treatment, and "CHase" denotes chondroitinase ABC treatment (FIGS. 7A-7F)
Figure 7A:
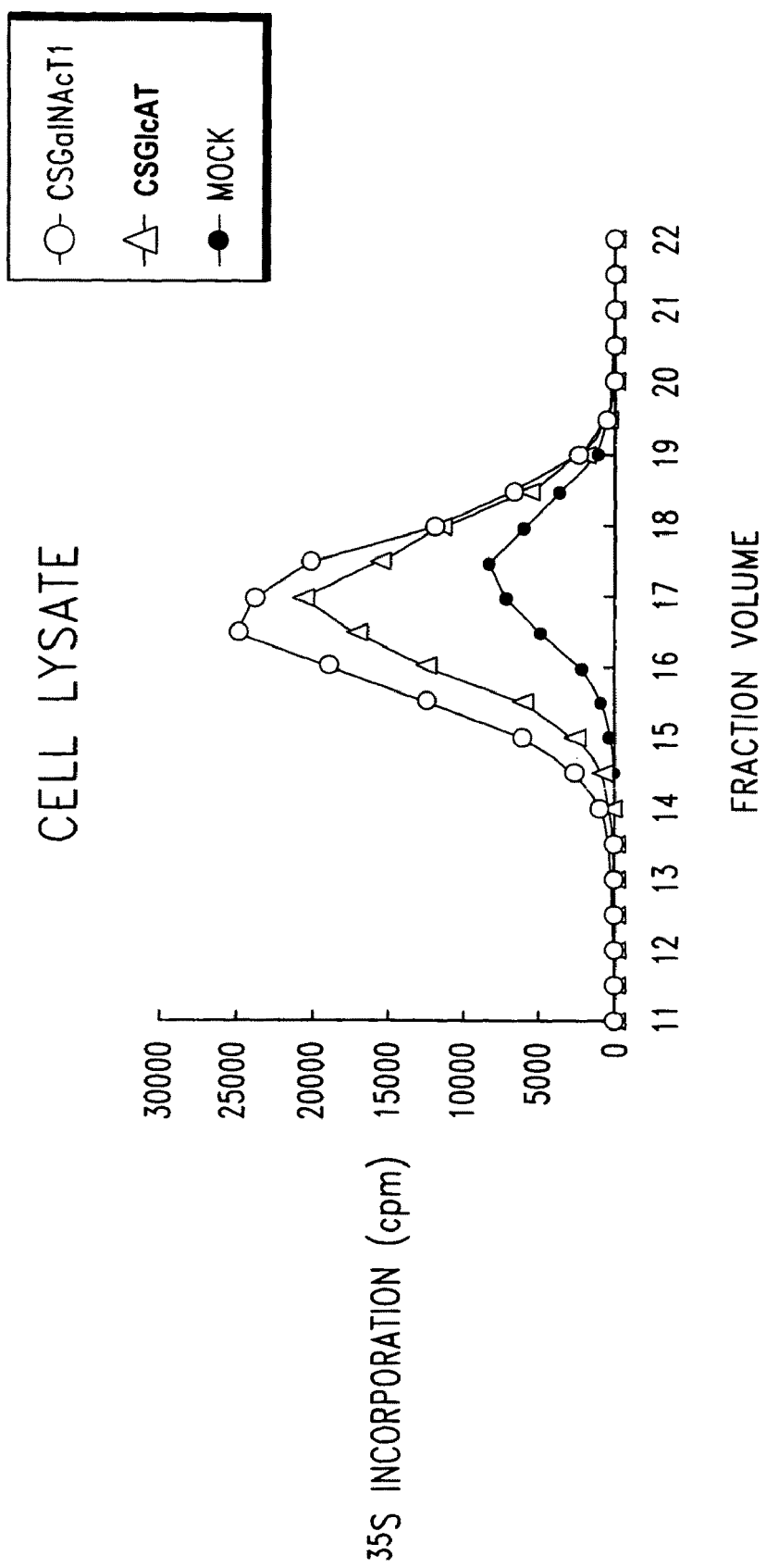
Figure 7B:
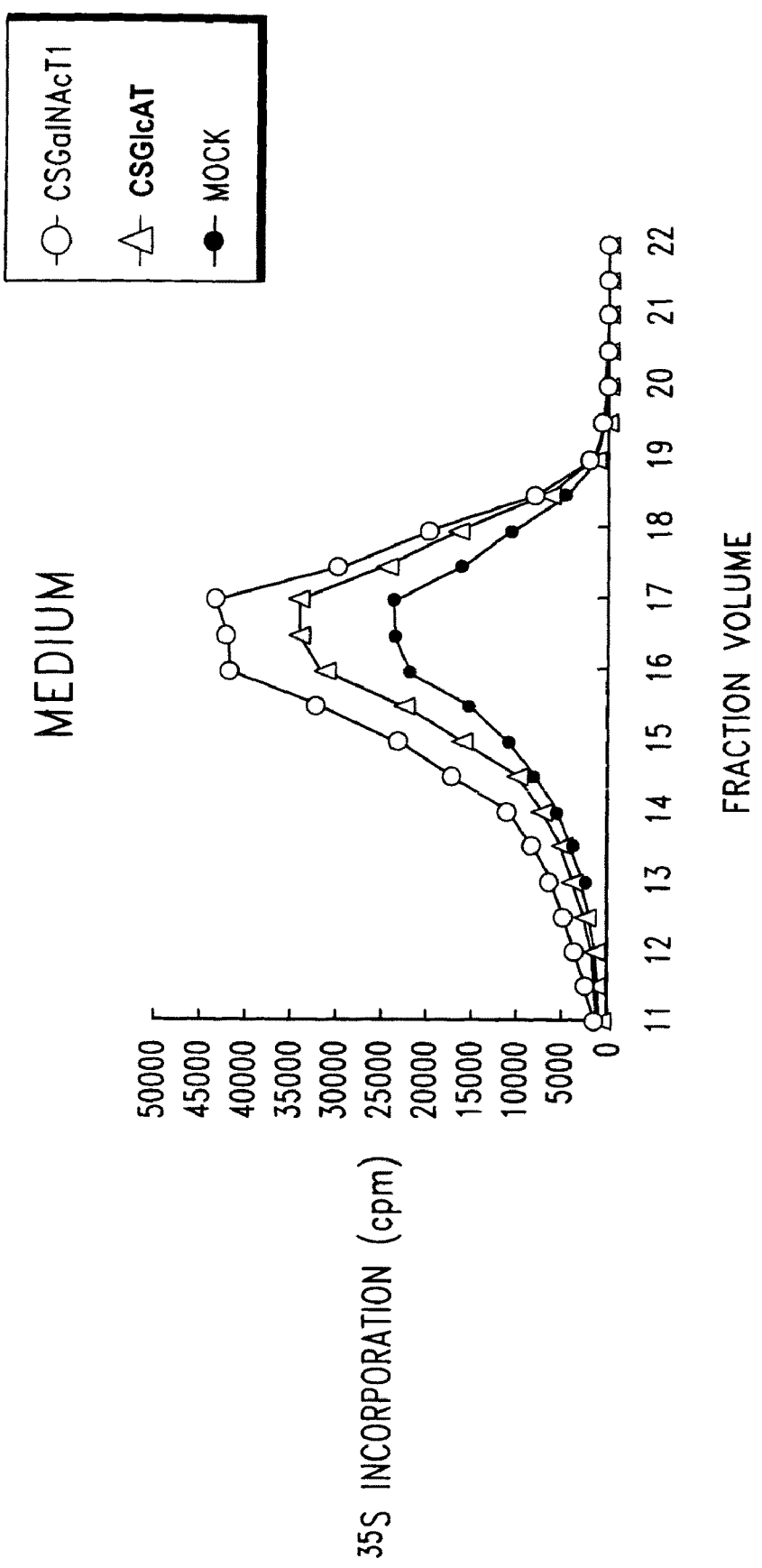

The graph in FIG. 7 shows scintillation counts (transfected cell lysate and culture medium) of digested chondroitin sulfate fractions (19.5 mL to 21 mL) obtained from chondroitinase ABC-treated samples (graphs in FIGS. 7A-7F elution curve graphs). Each scintillation count is a sum of the count attributed to the respective transfected cells and that attributed to the respective culture medium.

(4) Disaccharide Analysis of Chondroitinase-ABC Digests of GAG Samples:

With reference to a method disclosed in Analytical Biochemistry, 177, 327-332 (1989), chondroitinase-ABC-digested products of glycosaminoglycan chains synthesized by the transfected cells were analyzed in terms of disaccharide composition.

LTC cells transfected with a CSGlcAT gene and those transfected with a CSGalNAcT-1 gene were cultured in cell culture dishes (3003, product of Falcon) containing a DMEM medium supplemented with 10% FBS, penicillin, and streptomycin, at 37° C. under 5% CO2 for 24 hours. Subsequently, cells and a culture medium were separately collected and extracted 0.1-mol/L sodium hydride solution at 4° C. for 16 hours. Subsequently, the system was neutralized with 4-mol/L acetic acid. Under 20-mmol/L Tris-HCl (pH: 8.0) buffered conditions, 5-μL protein kinase K (20 mg/mL, product of Roche) was added to the system, followed by treating at 37° C. for 12 hours. Through heating to 100° C., protein kinase K was inactivated. Then, 10-μL DNaseI (10 mg/mL, product of Boehringer Mannheim) and 10-μL RNaseA (10 mg/mL, product of Wako) were added to the above system, followed by treating at 37° C. for two hours. Glycosaminoglycan (GAG) chains were collected from the reaction mixture. The thus-collected GAG chains were applied to a DEAE-Sepharose column. The column was washed with a 0.2-mol/L aqueous sodium chloride solution, and GAG fractions were eluted with an aqueous 2-mol/L sodium chloride solution. The thus-obtained GAG was precipitated with a 1.3% aqueous potassium acetate solution and 95% ethanol, and the thus-obtained precipitate was suspended in a buffer (50-mmol/L Tris-HCl (pH: 7.5)-0.2-mol/L sodium chloride). The GAG suspension was treated with a chondroitinase ABC (product of SEIKAGAKU CORPORATION).

Figure 8:
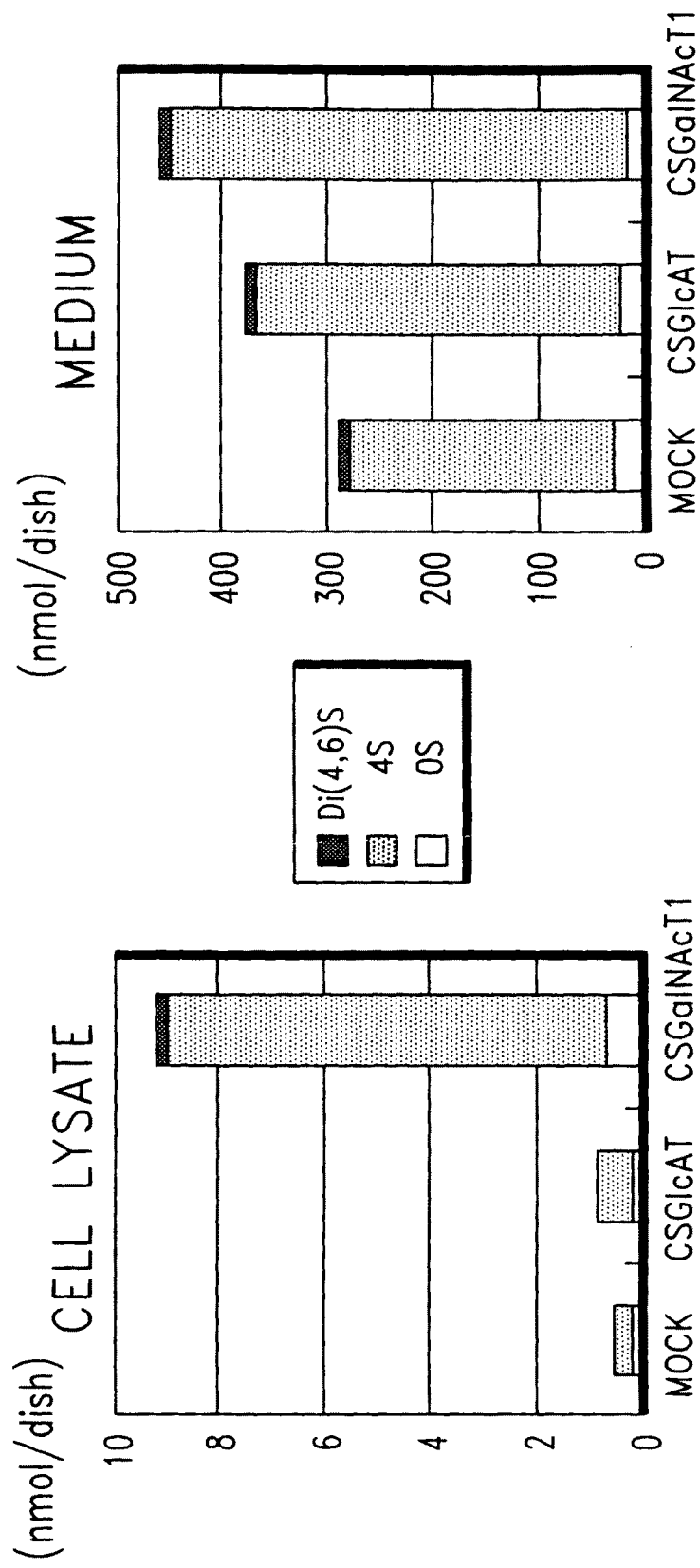
FIG. 8 shows results of disaccharide analysis of GAG digested products formed through chondroitinase ABC treatment of control (Mock) and sample of transfected cells, the disaccharide composition being determined in culture media and cell lysates (FIGS. 8A-8F)
Figure 8A:
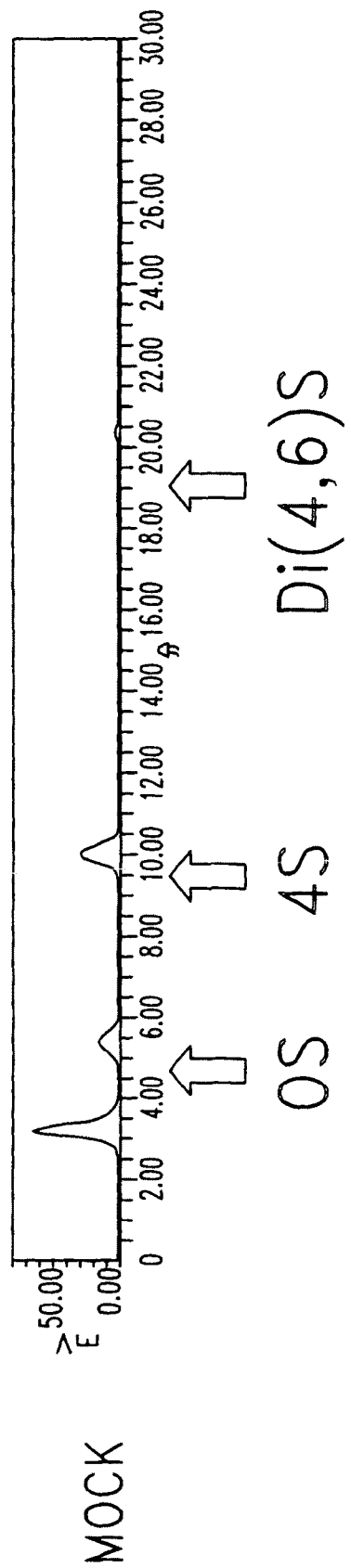
Figure 8B:
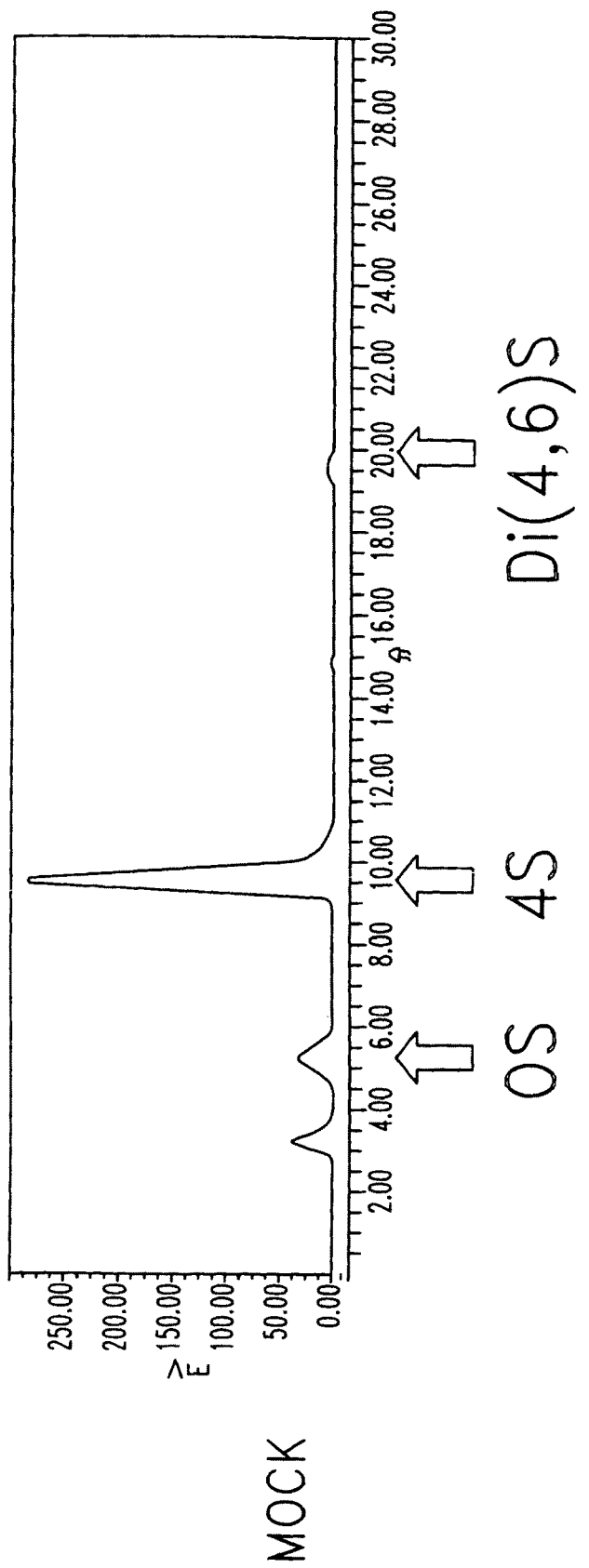
Figure 8C:
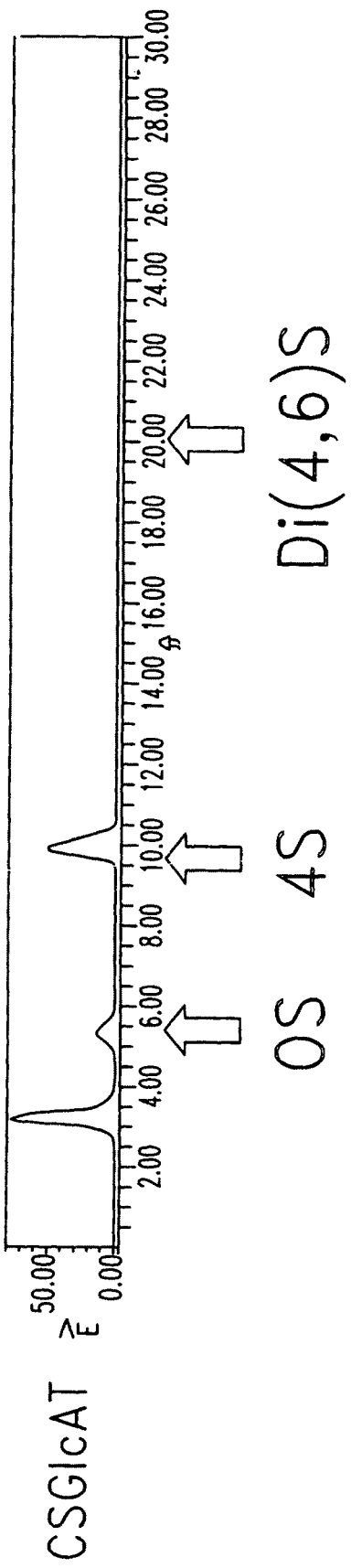
Figure 8D:
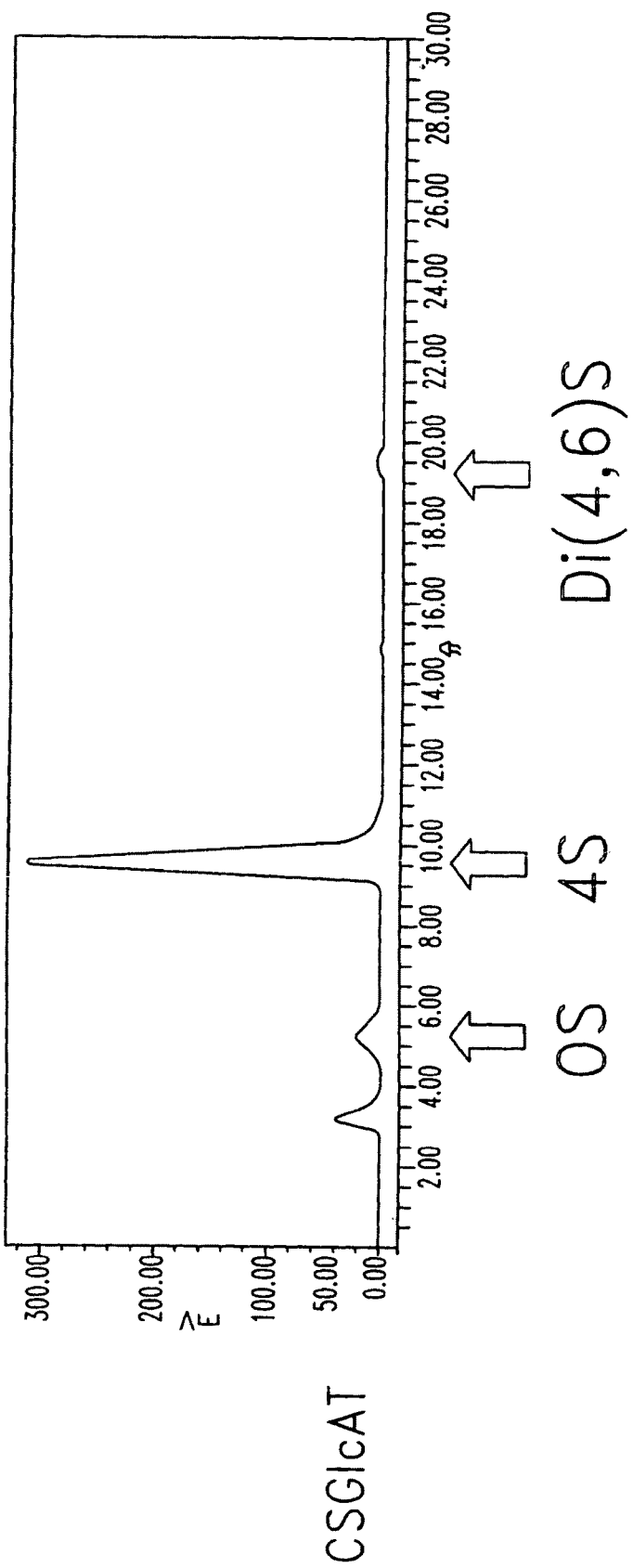
Figure 8E:
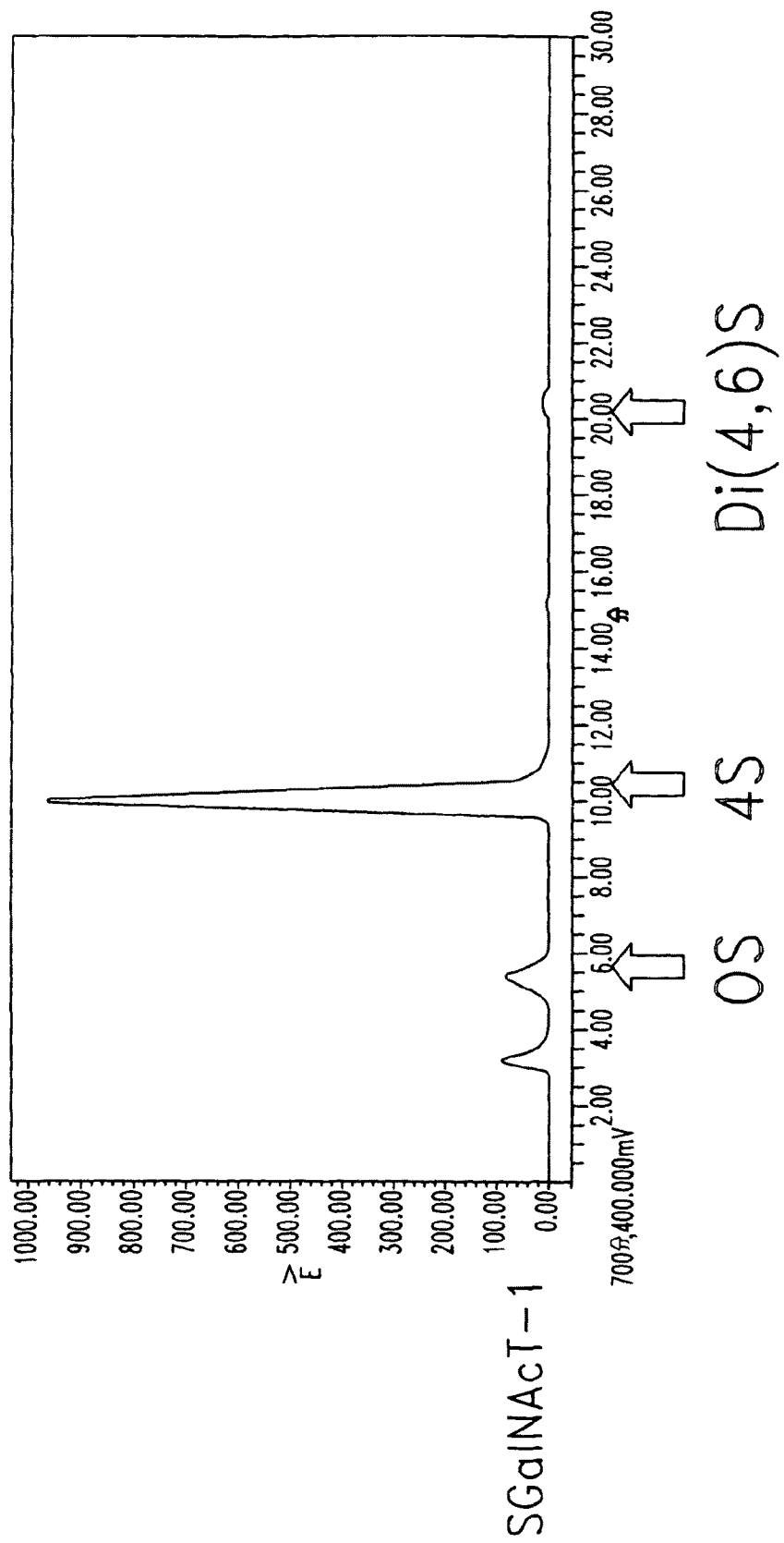
Figure 8F:
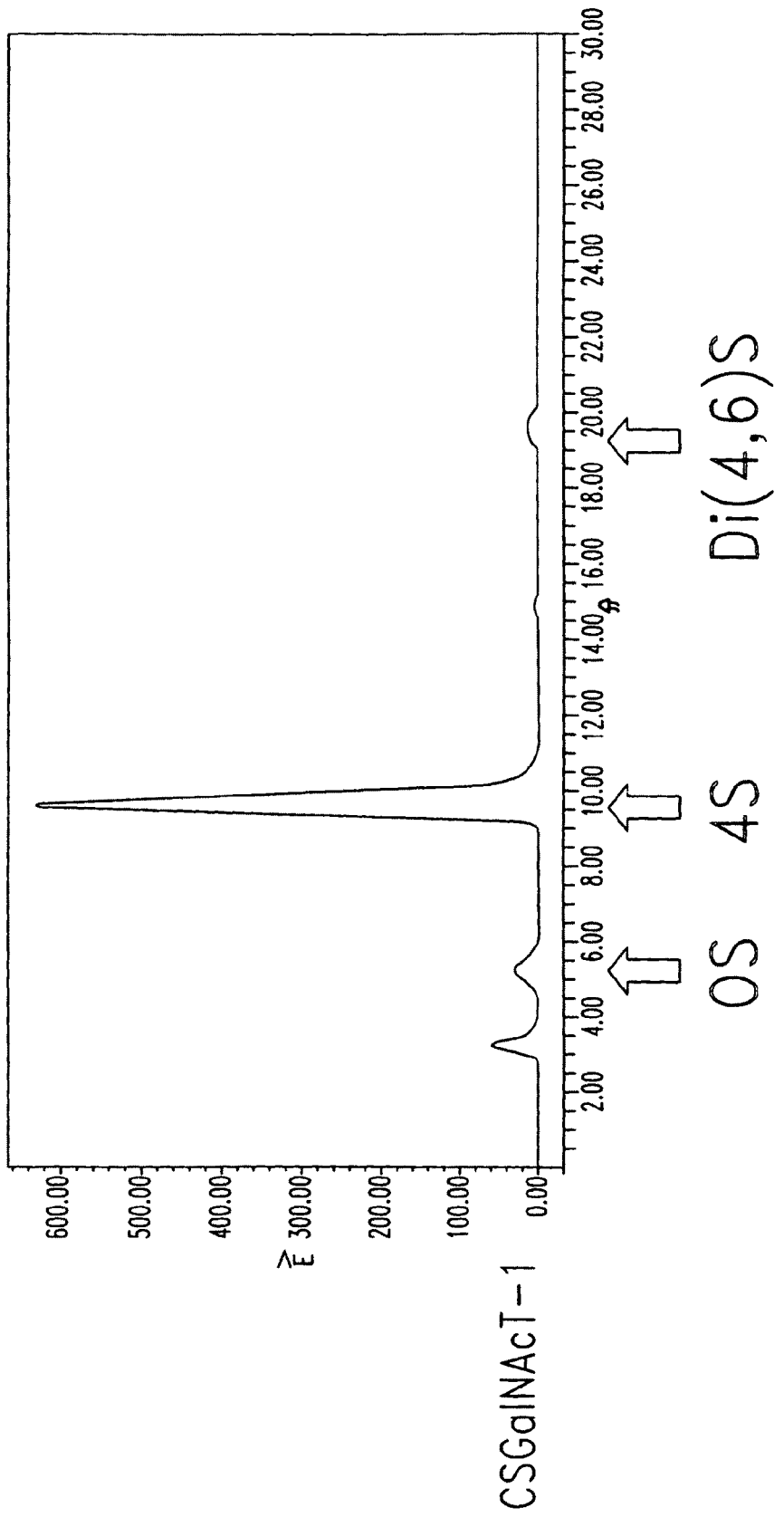

GAG-digested products formed through chondroitinase ABC treatment were analyzed through fluorometric postcolumn HPLC so as to confirm presence of disaccharide (FIG. 8).

The graphs in FIG. 8 shows total peak area of the respective sugar with respect to Mock, CSGlcAT, and CSGalNAcT-1 obtained in disaccharide analysis (see FIGS. 8A-8F). Each bar shows the sum of peak areas (0S, 4S, and Di(4,6)S). The values were standardized on the basis of a peak area obtained from a disaccharide standard sample (10 μmol/L) through the same method, and were reduced to amount of GAG/dish.

As used herein, "Di(4,6)S" denotes an unsaturated disaccharide which forms a disaccharide unit of chondroitin sulfate and which has a 4-sulfate group and 6-sulfate group (instead of 4-hydroxyl group and 6-hydroxyl group) in N-acetylgalactosamine; "4S" denotes an unsaturated disaccharide which forms the disaccharide unit and which has only a 4-sulfate group in N-acetylgalactosamine; and "0S" denotes an unsaturated disaccharide having no sulfate unit in the disaccharide unit.

In analysis (1) above, CSGlcAT-transfected cells and CSGalNAcT-1-transfected cells exhibited a remarkably high expression of the introduced genes, as compared with the control.

In immunostaining analysis (2) above, as compared with the control (Mock), CSGlcAT-transfected cells and CSGalNAcT-1-transfected cells have higher chondroitin 4-sulfate contents, and have an aggrecan core protein content almost equivalent to that of the control. The LTC cells are maturation chondrocytes, and cell characteristics remain during continuous culturing. In other words, the LTC cells constantly synthesize predetermined aggrecan molecules. Consequently, the core protein amount of aggrecan was found to be constant.

In analysis (3) above, transfected cells overexpressing CSGlcAT and CSGalNAcT-1 exhibited chondroitin sulfate synthesis activity of 1.6 fold and 2.2 fold, respectively, as compared with the control. As shown in the graph in FIG. 7 (middle, right), chondroitin sulfate elution curves of Mock, CSGlcAT, and CSGalNAcT-1-transfected cells, which had been treated with the heparitinase mixture, exhibited a common peak profile corresponding to fractions. Therefore, the synthesized chondroitin sulfate chains released to the culture medium had no variation in size among samples.

The above analyses revealed that, in CSGlcAT-transfected cells and CSGalNAcT-1-transfected cells, the amount of aggrecan core protein was not changed, but chondroitin sulfate chains of the same length were synthesized 1.6 fold and 2.2 fold in amount, respectively, indicating that the number of chondroitin sulfate chains in one aggrecan molecule increased 1.6 fold and 2.2 fold, respectively.

In analysis (4), chondroitin sulfate synthesized in each transfected cells exhibited a large amount of disaccharide essential units having a 4-sulfate structure. As compared with CSGlcAT-transfected cells, CSGalNAcT-1-transfected cells synthesized chondroitin sulfate in a larger amount.

Examples 2, 3, and 4 have revealed that, among chondroitin sulfate glycosyltransferases believed to be related to biosynthesis of chondroitin sulfate, CSGlcAT and CSGalNAcT-1 are closely related to biosynthesis of chondroitin sulfate in cartilage. In particular, CSGalNAcT-1 is closely related to the biosynthesis. The Examples have also revealed that an increase in expression levels of CSGlcAT and CSGalNAcT-1 leads to an increase in amounts of chondroitin sulfate chains bound to the core protein of one aggrecan molecule, as compared with the control.

Accordingly, when expression or activity of these enzymes is promoted, or these enzymes are exogenously administered, synthesis of chondroitin sulfate chains is expected to be promoted in cartilage, whereby the number of chondroitin sulfate chains which forms parts of aggrecan can be increased.

Example 7

Biosynthesis of Chondroitin Sulfate (CS) in Mouse Intervertebral Discs by In Vivo Gene Delivery of CSGalNAcT-1 cDNA encoding hCSGalNAcT-1 (CSGalNAcT-1 of human origin) was prepared by PCR using primers (5'-CACCATGATGATGGTTCGCCG-3' SEQ ID NO: 38, 5'-TGTTTTTTTGCTACTTGTCTTCTG-3' SEQ ID NO: 39) and a plasmid (hCSGalNAcT-1/pcDNA3.1) as a template, and the prepared cDNA was subcloned into adenoviral expression vectors (pAd/CMV/V5-DEST, manufactured by Invitrogen, Co.) through entry-vectors (pENT/D-TOPO, manufactured by Invitrogen, Co.) to obtain adenoviral vectors for expression of hCSGa1NAcT-1. Next, the adenoviral vectors for expression of hCSGalNAcT-1 were transduced into 293A cells (manufactured by Invitrogen, Co.) using an ViraPower Adenovirus Expression System (manufactured by Invitrogen, Co.) according to the manufacturer's instructions to obtain adenoviral particles for expression of hCSGalNAcT-1.

The particles' titer was checked according to the above manufacturer's instructions. 1.5×10⁷ plaque-forming unit (pfu) ADENOVIRAL particles were dissolved in 30 μl phosphate buffer saline and injected into mouse intervertebral discs of 4 month old ICR mice at a dosage of 1.5×10⁷ plaque-forming unit (pfu). In addition, adenoviral particles were prepared with pAd/CMV/V5-GW/Lac-Z (manufactured by Invitrogen, Co.) according to the above-described same procedures and used as a negative control ("mock").

Figure 10:
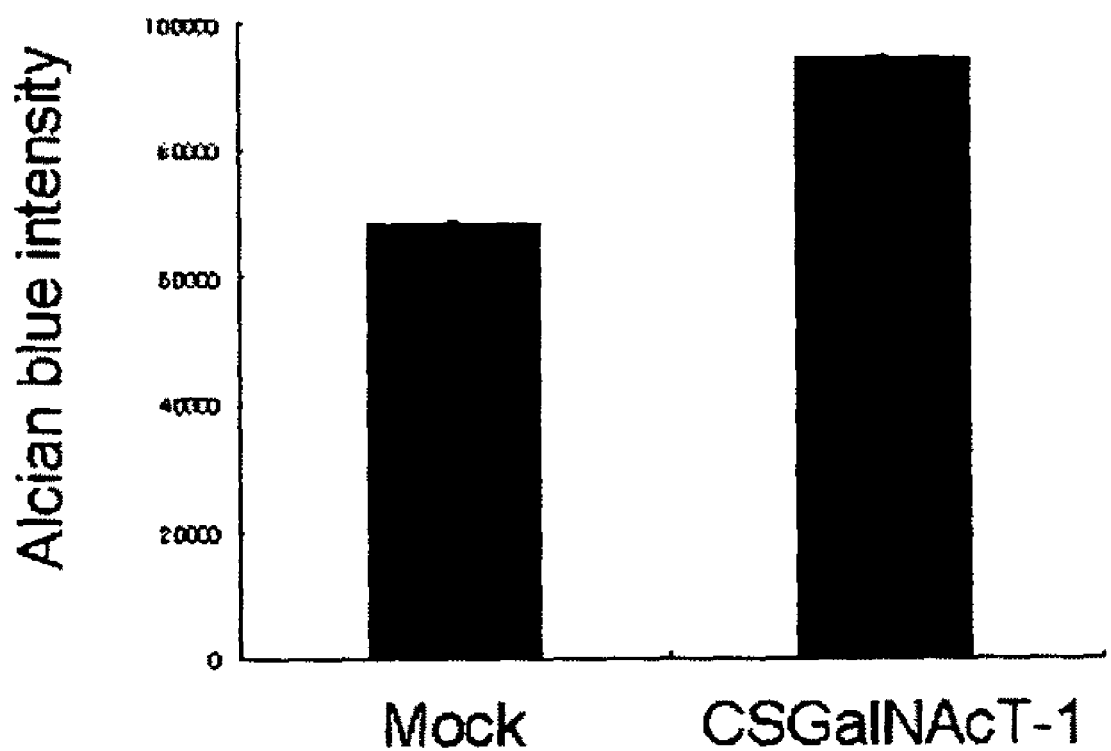
FIG. 10 shows levels for alcian blue stain of intervertebral disc in transgenic mice for CSGalNAcT-1.

At day 7 after the injection the mice were dissected and the intervertebral discs were stained with alcian blue. Quantitative imaging by NIH-image (produced by National Institute of Health) were then performed on the results of alcian blue stain and the alcian blue stain were figured in quantitative data (FIG. 10).

Figure 9:
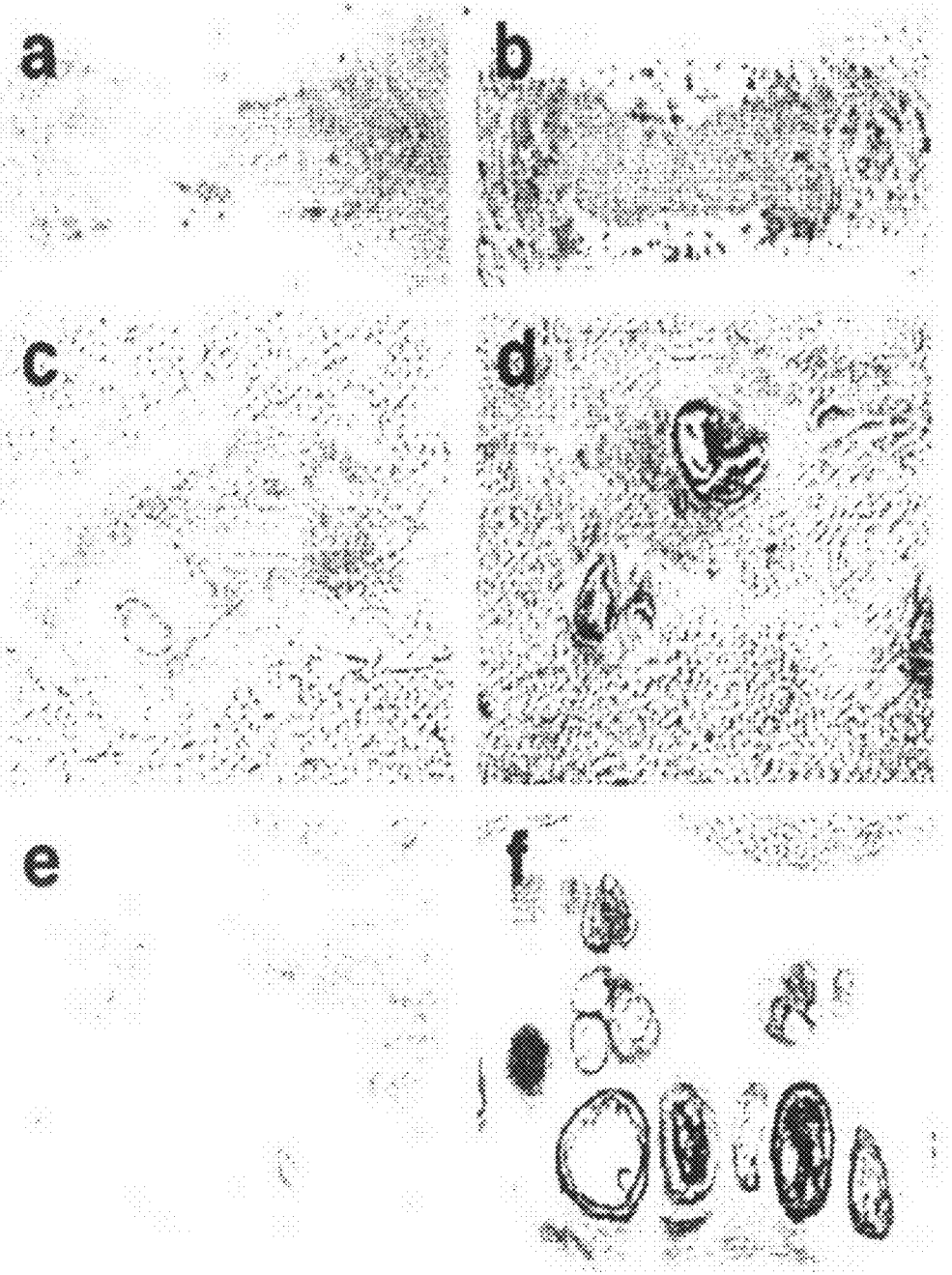
FIG. 9 shows results of Alcian Blue staining of intervertebral disc in transgenic mice for CSGalNAcT-1 (photographs), wherein the photographs of a, c and e are for the mock, the photographs of b, d and f are for the transgenic mice, a and b are the overall view for the intervertebral disc, c and d are closeups for the nucleus pulposus cells and e and f are close-ups for the chondrocytes.

Histological analysis showed intense alcian blue staining in the pericellular zone of the nucleus pulposus cells in the disc and chondrocytes in the vertebral endplate of the mice injected with the CSGalNAcT-1 gene, compared to that of mice injected with the mock (FIG. 9). This result teaches that the volume or biosynthesis of CS in mouse intervertebral discs is increased by in vivo gene delivery of CSGalNAcT-1.

And upon the above, it is asserted that genetic therapy with delivery of the gene of CSGalNAcT-1 into a joint increases the volume of CS in that joint toward attacking and/or curing diseases or symptoms associated with the decrease of the volume of CS.

Results in the present invention teach that the introduction of CSGalNAcT-1 gene and/or CSGlcAT gene, or exogenous administration of CSGalNAcT-1 protein and/or CSGlcAT protein promotes expression or activity of these enzymes in joints such as cartilage or intervertebral disc. Then the synthesis of chondroitin sulfate chain can be promoted, resulting in an increase of chondroitin sulfate chains of aggrecan.

In addition, it is believed that improved water retention of aggrecan by virtue of an increase in chondroitin sulfate chains, improves functions of cartilage and imparts an increase in shock absorbing and friction reducing (lubrication) performance there to. When expression or activity of these enzymes is promoted, or these enzymes are exogenously administered, formation of cartilage is expected to be promoted. For example, a cartilage formation promoter and a cartilage repairing agent for repairing damaged cartilage can be provided. Through employment of a drug or drug treatment comprising CSGalNAcT-1 or CSGlcAT as an active ingredient, or a genetic therapy employing a gene encoding CSGalNAcT-1 or CSGlcAT, a cartilage repairing agent or a treatment agent for articular disease and discopathy can be effectively provided.

What is claimed is:

1. A method for promoting chondroitin sulfate synthesis in a living subject wherein the living subject is a joint, a cartilage, or an intervertebral disc, the method comprising the steps of:
   providing a nucleic acid encoding chondroitin sulfate N-acetylgalactosaminyltransferase-1 and having a nucleotide sequence defined by SEQ. ID NO: 3; and
   introducing the nucleic acid into the living subject.

2. A method for promoting a chondroitin sulfate synthesis in a living subject as described in claim 1, wherein the step of introducing the nucleic acid into the living subject is performed with a gene gun or via injection.

3. A method for promoting a chondroitin sulfate synthesis in a living subject as described in claim 1, wherein the nucleic acid encodes a protein having activity of transferring an N-acetylgalactosamine residue from an N-acetylgalactosamine donor to a non-reducing end D-glucuronate residue of an N-acetylgalactosamine acceptor substrate containing a sugar chain represented by formula:

GlcUA-Gal-Gal-Xyl (wherein GlcUA represents a D-glucuronate residue, Gal represents a D-galactose residue, Xyl represents a D-xylose residue, and "-" represents a glycosidic linkage).

4. The method of claim 1 wherein the nucleic acid is introduced into an intervertebral disc of the living subject.

* * * * *